United States Patent
Ramachandran Iyer

(10) Patent No.: US 11,732,299 B2
(45) Date of Patent: Aug. 22, 2023

(54) SPATIAL ASSAYS WITH PERTURBED CELLS

(71) Applicant: 10x Genomics, Inc., Pleasanton, CA (US)

(72) Inventor: Eswar Prasad Ramachandran Iyer, Pleasanton, CA (US)

(73) Assignee: 10x Genomics, Inc., Pleasanton, CA (US)

(*) Notice: Subject to any disclaimer, the term of this patent is extended or adjusted under 35 U.S.C. 154(b) by 157 days.

(21) Appl. No.: 17/153,384

(22) Filed: Jan. 20, 2021

(65) Prior Publication Data

US 2021/0222242 A1 Jul. 22, 2021

Related U.S. Application Data

(60) Provisional application No. 62/963,879, filed on Jan. 21, 2020, provisional application No. 62/963,897, filed on Jan. 21, 2020.

(51) Int. Cl.
*C12Q 1/6874* (2018.01)

(52) U.S. Cl.
CPC .................. *C12Q 1/6874* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Vickovic et al., "Massive and parallel expression profiling using microarrayed single-cell sequencing," Nat. Commun. 2016, 7:13182. (Year: 2016).*
Adamson et al., "A Multiplexed Single-Cell CRISPR Screening Platform Enables Systematic Dissection of the Unfolded Protein Response," Cell 2016, 167:1867-1882. (Year: 2016).*
U.S. Appl. No. 16/353,937, filed Mar. 14, 2019, Frisen et al.
U.S. Appl. No. 17/707,189, filed Mar. 29, 2022, Chell et al.
Dalma-Weiszhausz et al., "The Affymetrix GeneChip platform: an overview," Methods Enzymol., 2006, 410:3-28.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

(Continued)

*Primary Examiner* — Kaijiang Zhang
(74) *Attorney, Agent, or Firm* — Fish & Richardson P.C.

(57) ABSTRACT

This disclosure relates to methods for spatial profiling of analytes present in a biological sample. Also provided are methods for using spatially barcoded arrays to detect a biological analyte in a cell comprising a small molecule.

24 Claims, 18 Drawing Sheets

(56) References Cited

U.S. PATENT DOCUMENTS

| | | |
|---|---|---|
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,677,160 B1 | 1/2004 | Stockman et al. |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,337,851 B2 | 12/2012 | Aukerman |
| 8,343,500 B2 | 1/2013 | Wraith |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |

(56) References Cited

U.S. PATENT DOCUMENTS

| | | |
|---|---|---|
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,266,876 B2 | 4/2019 | Cai et al. |
| 10,267,808 B2 | 4/2019 | Cai |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 2001/0055764 A1 | 12/2001 | Empedocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0087232 A1 | 5/2003 | Christians |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |

(56) References Cited

U.S. PATENT DOCUMENTS

| | | |
|---|---|---|
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0289184 A1 | 11/2009 | Deininger |
| 2009/0291854 A1 | 11/2009 | Wiesinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mita et al. |
| 2010/0145037 A1 | 6/2010 | Brive et al. |
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0223613 A1 | 9/2011 | Gut |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mita et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0065609 A1 | 3/2014 | Hicks et al. |
| 2014/0066318 A1 | 3/2014 | Frisen et al. |
| 2014/0121118 A1 | 5/2014 | Warner |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0242020 A1 | 8/2017 | Yamauchi et al. |
| 2017/0335297 A1 | 11/2017 | Ha et al. |
| 2017/0335410 A1 | 11/2017 | Driscoll et al. |
| 2017/0343545 A1 | 11/2017 | Hadrup et al. |
| 2017/0349940 A1 | 12/2017 | Morin et al. |

(56) References Cited

U.S. PATENT DOCUMENTS

| | | |
|---|---|---|
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0105808 A1 | 4/2018 | Mikkelsen et al. |
| 2018/0112261 A1 | 4/2018 | Van Driel et al. |
| 2018/0114316 A1 | 4/2018 | Lele et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251825 A1 | 9/2018 | Stoeckius et al. |
| 2018/0282803 A1 | 10/2018 | Belgrader et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0346970 A1 | 12/2018 | Chang |
| 2019/0055594 A1 | 2/2019 | Samusik et al. |
| 2019/0064173 A1 | 2/2019 | Bharadwaj et al. |
| 2019/0085324 A1 | 3/2019 | Regev et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0352708 A1 | 11/2019 | Gaige et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0002764 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava et al. |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |

(56) References Cited

U.S. PATENT DOCUMENTS

| | | | |
|---|---|---|---|
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| RU | 2270254 | 2/2006 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2000/024940 | 5/2000 |
| WO | WO 2001/06012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/117541 | 11/2006 |
| WO | WO 2006/124771 | 11/2006 |
| WO | WO 2007/030373 | 3/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2012/048341 | 4/2012 |
| WO | WO 2012/049316 | 4/2012 |
| WO | WO 2012/071428 | 5/2012 |
| WO | WO 2012/083225 | 6/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/130576 | 8/2014 |

(56) References Cited

FOREIGN PATENT DOCUMENTS

| | | |
|---|---|---|
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/031691 | 3/2015 |
| WO | WO 2015/069374 | 5/2015 |
| WO | WO 2015/161173 | 10/2015 |
| WO | WO 2016/040476 | 3/2016 |
| WO | WO 2016/057552 | 4/2016 |
| WO | WO 2016/077763 | 5/2016 |
| WO | WO 2016/126871 | 8/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075265 | 5/2017 |
| WO | WO 2017/075293 | 5/2017 |
| WO | WO 2017/096158 | 7/2017 |
| WO | WO 2017/143155 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/075693 | 4/2018 |
| WO | WO 2018/085599 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/077236 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | Wo 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/086880 | 5/2023 |

OTHER PUBLICATIONS

Lahiani et al., "Enabling Histopathological Annotations on Immunofluorescent Images through Virtualization of Hematoxylin and Eosin," J Pathol Inform., Feb. 2018, 9:1, 8 pages.

Lou et al., "A review of room temperature storage of biospecimen tissue and nucleic acids for anatomic pathology laboratories and biorepositories," Clin Biochem., Mar. 2014, 47(4-5):267-73.

Lykidis et al., "Novel zinc-based fixative for high quality DNA, RNA and protein analysis," Nucleic Acids Res., Jun. 2007, 35(12):e85, 10 pages.

Madissoon et al., "ScRNA-seq assessment of the human lung, spleen, and esophagus tissue stability after cold preservation," Genome Biol., Dec. 2019, 21(1):1, 16 pages.

(56) References Cited

OTHER PUBLICATIONS

Miller et al., "Chapter 11—Solid and Suspension Microarrays for Microbial Diagnostics," Methods in Microbiology, 2015, 42:395-431.
Nadji et al., "Immunohistochemistry of tissue prepared by a molecular-friendly fixation and processing system," Appl Immunohistochem Mol Morphol., Sep. 2005, 13(3):277-82.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Vickovic et al., "SM-Omics: An automated Platform for High-Throughput Spatial Multi-Omics," bioRxiv, Oct. 2020, 40 pages.
Wang et al., "Optimization of Process Conditions for Infected Animal Tissues by Alkaline Hydrolysis Technology," Procedia Environmental Sciences, 2016, 31:366-374.
Wohnhaas et al., "DMSO cryopreservation is the method of choice to preserve cells for droplet-based single-cell RNA sequencing," Scientific Reports, Jul. 2019, 9(1):10699, 14 pages.
U.S. Appl. No. 60/416,118, filed Oct. 3, 2002, Fan et al.
U.S. Appl. No. 61/267,363, filed Dec. 7, 2009, Fan et al.
U.S. Appl. No. 62/946,885, filed Dec. 11, 2019, Clark et al.
[No Author Listed], "Chromium Next GEM Single Cell 3' Reagent Kits v3.1," User Guide, Document No. CG000204, 10x Genomics, Nov. 2019, 58 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersbam Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf, 43 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GaT Mismatches in DNA," Biochemistry, 1996, 36(34):10581-10594.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andresen et al., "Helicase-dependent amplification: use in OnChip amplification and potential for point-of-care diagnostics," Expert Rev Mol Diagn., Oct. 2009, 9(7):645-650.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology. 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Behzadi et al., "Cellular uptake of nanoparticles: journey inside the cell," Chem Soc Rev., Jul. 2017, 46(14):4218-4244.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolognesi et al., "Multiplex Staining by Sequential Immunostaining and Antibody Removal on Routine Tissue Sections," J. Histochem. Cytochem., Aug. 2017, 65(8):431-444.
Boutros et al., "The art and design of genetic screens: RNA interference," Nat Rev Genet., Jul. 2008, 9(7):554-66.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.

(56) References Cited

OTHER PUBLICATIONS

Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chen et al., "ATAC-see reveals the accessible genome by transposase-mediated imaging and sequencing," Nature Methods, Dec. 2016, 13(12):1013-1020.
Cheng et al., "Sensitive Detection of Small Molecules by Competitive Immunomagnetic-Proximity Ligation Assay," Anal Chem, 2012, 84:2129-2132.
Chrisey et al., "Covalent attachment of synthetic DNA to self-assembled monolayer films," Nucleic Acids Res., Aug. 1996, 24(15):3031-9.
Chung et al., "Structural and molecular interrogation of intact biological systems," Nature, May 2013, 497:332-337.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Corces et al., "Lineage-specific and single-cell chromatin accessibility charts human hematopoiesis and leukemia evolution," Nature Genetics, Oct. 2016, 48(10):1193-1203.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.

Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Dandapani et al., "Selecting, Acquiring, and Using Smail Molecule Libraries for High-Throughput Screening," Curr Protoc Chem Biol., Sep. 2012, 4:177-191.
Darmanis et al., "ProteinSeq: High-Performance Proteomic Analyses by Proximity, Ligation and Next Generation Sequencing," PLos One, 2011, 6(9):e25583, 10 pages.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identity chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dixit el al., "Perturb-Seq: Dissecting Molecular Circuits with Scalable Single-Cell RNA Profiling of Pooled Genetic Screens," Cell, Dec. 2016, 167(7):1853-1866.e17.
Donahue et al., "Concepts of nanoparticle cellular uptake, intracellular trafficking, and kinetics in nanomedicine," Adv Drug Deliv Rev., Mar. 2019, 143:68-96.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.

(56) References Cited

OTHER PUBLICATIONS

Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gierahn et al., "Seq-Well: portable, low-cost RNA sequencing of single cells at high throughput," Research Square, 2017, 53 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hahnke et al., "Striptease on glass: validation of an improved stripping procedure for in situ microarrays," J Biotechnol., Jan. 2007, 128(1):1-13.
Hajduk et al., "Drug discovery: A question of library design," Nature, Feb. 2011, 470(7332):42-43.
Hammond et al., "Profiling cellular protein complexes by proximity ligation with dual tag microarray readout," PLoS ONE, 2012, 7(7):e40405, 9 pages.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Harris et al., "The design and application of target-focused compound libraries," Comb Chem High Throughput Screen, Jul. 2011, 14(6):521-531.
He et al., "In situ synthesis of protein arrays." Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencinq," PLoS One, 5(7):e11345, 2010.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "Dissecting Cell-Type Composition and Activity-Dependent transcriptional State in Mammalian Brains by Massively Parallel Single-Nucleus RNA-Seq." Mol Cell., Dec. 2017, 68(5):1006-1015.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jabara et al., Accurate sampling and deep sequencing of the HIV-1 protease gene using a Primer ID. PNAS 108(50); 20166-20171, 2011.
Jahangirian et al., "A review of small molecules and drug delivery applications using gold and iron nanoparticles," Int J Nanomedicine, Mar. 2019, 14:1633-1657.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jones et al., "Comparative lesion sequencing provides insights into tumor evolution," Proc. Natl. Acad. Sci. USA, 105(11): 4283-4288, 2008.
Kainkaryam et al., "Pooling in high-throughput drug screening" Curr Opin Drug Discov Devel., May 2009, 12(3):339-50.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.

(56) References Cited

OTHER PUBLICATIONS

Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Liberali et al., "Single-cell and multivariate approaches in genetic perturbation screens," Nat Rev Genet., Jan. 2015, 16(1):18-32.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Lino et al., "Delivering CRISPR: a review of the challenges and approaches," Drug Deliv., Nov. 2018, 25(1):1234-1257.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyck et al., "Immunohistochemical markers for quantitative studies of neurons and glia in human neocortex," J Histochem Cytochem, 2008, 56(3):201-21.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
McDade et al., "Practical Considerations for Using Pooled Lentiviral CRISPR Libraries," Curr Protoc Mol Biol., Jul. 2016, 115:31.5.1-31.5.13.
Meers et al., "Improved CUT&RUN chromatin profiting tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.

(56) References Cited

OTHER PUBLICATIONS

Mortazavi et al., "Mapping and quantifying mammalian transcriptomes by RNA-Seq," Nature Methods, 5(7): 621-8, 2008.
Mosquera et al., "Cellular Uptake of Nanoparticles versus Small Molecules: A Matter of Size," Acc Chem Res., Sep. 2018, 51(9):2305-2313.
Motea et al., "Terminal deoxynucleotidyl transferase: the story of a misguided DNA polymerase," Biochim Biophys Acta., May 2010, 1804(5):1151-66.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem. May 1995, 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of Ap5A," FEBS Lett., Mar. 1987, 213(1):204-8.
Paricharak et al., "Data-driven approaches used for compound library design, hit triage and bioactivity modeling in high-throughput screening." Brief Bioinform., Mar. 2018, 19(2):277-287.
Park et al., "Single cell trapping in larger microwells capable of supporting cell spreading and proliferation," Microfluid Nanofluid, 2010, 8:263-268.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tcl/mariner transposon family," Curr Top Microbiol Immunol., 1996, 204:125-43.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Satpathy et al., "Massively parallel single-cell chromatin landscapes of human immune cell development and intratumoral T cell exhaustion," Nat Biotechnol, Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Setliff et al., High-Throughput Mapping of B Cell Receptor Sequences to Antigen Specificity, Cell, 2019, 179:1636-1646.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Stuart et al., "Comprehensive Integration of Single-Cell Data," Cell, Jun. 2019, 177(7):1888-1902.
Tang et al., "RNA-Seq analysis to capture the transcriptome landscape of a single cell.," Nat Protoc., 5:516-35, 2010.

(56) References Cited

OTHER PUBLICATIONS

Taniguchi et al., "Quantitative analysis of gene expression in a single cell by qPCR," Nature Methods, 6, pp. 503-506, 2009.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nature Methods, 2019, 9 pages.
Vickovic et al., "Massive and parallel expression profiling using microarrayed single-cell sequencing," Nature Communications, 2016, 7(13182):1-9.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics,'" Trends Biotechnol., 28: 281-90, 2010.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.

Wheeler et al., "Microfluidic device for single-cell analysis," Analytical Chemistry, Jul. 2003, 75(14):3581-3586.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yamauchi et al., "Subcellular western blotting of single cells," Microsyst Nanoeng., 2017, 3:16079, 9 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "A comparison between sphere and rod nanoparticles regarding their in vivo biological behavior and pharmacokinetics," Scientific Reports, Jun. 2017, 7(1):4131, 11 pages.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Alam, "Proximity Ligation Assay (PLA)," Curr Protoc Immunol., Nov. 2018, 123(1):e58, 8 pages.
Azioune et al., "Simple and rapid process for single cell micropatterning," Lab Chip, Jun. 2009, 9(11):1640-1642.
Chen et al., "Geometric control of cell life and death," Science, May 1997, 276(5317):1425-1428.
Chung et al., "Imaging single-cell signaling dynamics with a deterministic high-density single-cell trap array," Anal Chem, Sep. 2011, 83(18):7044-7052.
Collins et al., "Two-dimensional single-cell patterning with one cell per well driven by surface acoustic waves," Nature Communications, Nov. 2015, 6:8686, 11 pages.
Ding et al., "On-chip manipulation of single microparticles, cells, and organisms using surface acoustic waves," PNAS, Jul. 2012, 109(28):11105-11109.
Falconnet et al., "Surface engineering approaches to micropattern surfaces for cell-based assays," Biomaterials, Jun. 2006, 27(16):3044-3063.

(56) References Cited

OTHER PUBLICATIONS

Folch et al., "Microfabricated elastomeric stencils for micropatterning cell cultures," J Biomed Mater Res, Nov. 2000, 52(2):346-353.
Giam et al., "Scanning probe-enabled nanocombinatorics define the relationship between fibronectin feature size and stem cell fate," PNAS, Mar. 2012, 109(12):4377-4382.
Gross et al., "Technologies for Single-Cell Isolation," Int. J Mol. Sci., Jul. 2015, 16(8):16897-16919.
Laurell et al., "Chip integrated strategies for acoustic separation and manipulation of cells and particles," Chem. Soc. Rev., Mar. 2007, 36(3):492-506.
Li et al., "An activity-dependent proximity ligation platform for spatially resolved quantification of active enzymes in single cells," Nat Commun, Nov. 2017, 8(1):1775, 12 pages.
Lin et al., "Microfluidic cell trap array for controlled positioning of single cells on adhesive micropatterns," Lab Chip, Feb. 2013, 13(4):714-721.
Nakamura et al., "Biocompatible inkjet printing technique for designed seeding of individual living cells," Tissue Eng, Nov. 2005, 11(11-12):1658-1666.
Ostuni et al., "Patterning Mammalian Cells Using Elastomeric Membranes," Langmuir, Aug. 2000, 16(20):7811-7819.
Rettig et al., "Large-scale single-cell trapping and imaging using microwell arrays," Anal Chem, Sep. 2005, 77(17):5628-5634.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rosenthal et al., "Cell patterning chip for controlling the stem cell microenvironment," Biomaterials, Jul. 2007, 28(21):3208-3216.
Suh et al., "A simple soft lithographic route to fabrication of poly(ethylene glycol) microstructures for protein and cell patterning," Biomaterials, Feb. 2004, 25(3):557-563.
Tan et al., "Parylene peel-off arrays to probe the role of cell-cell interactions in tumour angiogenesis," Integr Biol (Camb), Oct. 2009, 1(10):587-594.
Tseng et al., "Magnetic nanoparticle-mediated massively parallel mechanical modulation of single-cell behavior," Nat Methods, Nov. 2012, 9(11):1113-1119.
Vermesh et al., "High-density, multiplexed patterning of cells at single-cell resolution for tissue engineering and other applications," Angew Chem Int Ed Engl, Aug. 2011, 50(32):7378-7380.
Wiedmann et al., "Ligase chain reaction (LCR)—overview and applications," PCR Methods Appl., Feb. 1994, 3(4):S51-64.
Wood et al., "Single cell trapping and DNA damage analysis using microwell arrays," PNAS, Jun. 2010, 107(22):10008-10013.
Wright et al., "Reusable, reversibly sealable parylene membranes for cell and protein patterning," J Biomed Mater Res A., May 2008, 85(2):530-538.
Yusof et al., "Inkjet-like printing of single-cells," Lab Chip, Jul. 2011, 11(14):2447-2454.
Zhang et al., "Block-Cell-Printing for live single-cell printing," PNAS, Feb. 2014, 111(8):2948-2953.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Niedringhaus et al., "Landscape of next-generation sequencing technologies," Anal Chem., Jun. 2011, 83(12):4327-41.
Qiu et al., "Combination probes with intercalating anchors and proximal fluorophores for DNA and RNA detection," Nucleic Acids Research, Sep. 2016, 44(17):e138, 12 pages.
Zhao et al., "Isothermal Amplification of Nucleic Acids," Chemical Reviews, Nov. 2015, 115(22):12491-12545.
Asp et al., "Spatially Resolved Transcriptomes—Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Blair et al., "Microarray temperature optimization using hybridization kinetics," Methods Mol Biol., 2009, 529:171-96.
Bolotin et al., "MiXCR: software for comprehensive adaptive immunity profiling," Nat Methods., May 2015, 12(5):380-1.
Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase drain reaction," Anal Biochem, Mar. 1993, 209(2):284-90.
Ciaccio et al., "Systems analysis of EGF receptor signaling dynamics with microwestern arrays," Nat Methods, Feb. 2010, 7(2):148-55.
Gerard et al., "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000, 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Nam et al., "Somatic mutations and cell identity linked by Genotyping of Transcriptomes," Nature, Jul. 2019, 571(7765):355-360.
Nilsson et al., "RNA-templated DNA ligation for transcript analysis," Nucleic Acids Res., Jan. 2001, 29(2):578-81.
Olivier, "The Invader assay for SNP genotyping," Mutat. Res., Jun. 2005, 573(1-2):103-110.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perocchi et al., "Antisense artifacts in tianscriptome microarray experiments are resolved by actinomycin D," Nucleic Acids Res., 2007, 35(19):e128, 7 pages.
Picelli et al., "Full-length RNA-seq from single cells using Smart-seq2," Nat Protoc., Jan. 2014, 9(1):171-81.
Schouten et al., "Relative quantification of 40 nucleic acid sequences by multiplex ligation-dependent probe amplification," Nucleic Acids Res., Jun. 2002, 30(12):e57, 13 pages.
Singh et al., "High-throughput targeted long-read single cell sequencing reveals the clonal and transcriptional landscape of lymphocytes," Nat Commun., Jul. 2019, 10(1):3120, 13 pages.
Sountoulidis et al., "SCRINSHOT, a spatial method for single-cell resolution mapping of cell states in tissue sections," PLoS Biol., Nov. 2020, 18(11):e3000675, 32 pages.

(56) References Cited

OTHER PUBLICATIONS

Spiess et al., "A highly efficient method for long-chain cDNA synthesis using trehalose and betaine," Anal. Biochem., Feb. 2002, 301(2):168-74.
Sutherland et al., "Utility of formaldehyde cross-linking and mass spectrometry in the study of protein-protein interactions," J. Mass Spectrom., Jun. 2008, 43(6):699-715.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Tu et al., "TCR sequencing paired with massively parallel 3' RNA-seq reveals clonotypic T cell signatures," Nature Immunology, Dec. 2019, 20(12):1692-1699.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
U.S. Appl. No. 63/033,348, filed Jun. 2, 2020, Bent.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Baner et al., "Signal amplification of padlock probes by rolling circle replication," Nucleic Acids Res., 1998, 26(22):5073-5078.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
DePasquale et al., "DoubletDecon: Deconvoluting Doublets from Single-Cell RNA-Sequencing Data," Cell Rep., Nov. 5, 2019, 29(6):1718-1727.e8, 19 pages.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Faruqi et al., "High-throughput genotyping of single nucleotide polymorphisms with rolling circle amplification," BMC Genomics, Aug. 2001, 2:4, 10 pages.
Gao et al., "A highly homogeneous expansion microscopy polymer composed of tetrahedron-like monomers," bioRxiv, Oct. 22, 2019, 23 pages (Preprint).
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Goh et al., "Highly Specific Multiplexed RNA Imaging In Tissues With Split-FISH," Nat Methods, Jun. 15, 2020, 17(7):689-693, 21 pages.
Goransson et al., "A single molecule array for digital targeted molecular analyses," Nucleic Acids Res., Nov. 25, 2009, 37(1):e7, 9 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McGinnis et al., "MULTI-seq: sample multiplexing for single-cell RNA sequencing using lipid-tagged indices," Nat Methods, Jul. 2019, 16(7): 619-626, 14 pages.
Mignardi et al., "Oligonucleotide gap-fill ligation for mutation detection and sequencing in situ," Nucleic Acids Research, Aug. 3, 2015, 43(22):e151, 12 pages.
Mohsen et al., "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Stoeckius et al., "Cell Hashing with barcoded antibodies enables multiplexing and doublet detection for single cell genomics," Genome Biology, Dec. 19, 2018, 19: 224, 12 pages.
Takei et al., "Integrated Spatial Genomics Reveals Global Architecture Of Single Nuclei," Nature, Jan. 27, 2021, 590(7845):344-350, 53 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Zheng et al., "Massively parallel digital transcriptional profiling of single cells," Nat Commun., Jan. 16, 2017, 8:14049, 12 pages.
Hayes et al., "Electrophoresis of proteins and nucleic acids: I-Theory," BMJ, Sep. 1989, 299(6703):843-6.
[No Author Listed], "Chromium Next GEM Single Cell 3' Reagent Kits v3.1 (Dual Index)—User Guide," 10x Genomics, Mar. 2021, Document No. CG000315, 61 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdff>, 70 pages.
Blanco et al., "A practical approach to FRET-based PNA fluorescence in situ hybridization," Methods, Dec. 2010, 52(4):343-51.

(56) References Cited

OTHER PUBLICATIONS

Czarnik, "Encoding methods for combinatorial chemistry," Curr Opin Chem Biol., Jun. 1997, 1(1):60-6.
MacBeath et al., "Printing proteins as microarrays for high-throughput function determination," Science, Sep. 2000, 289(5485):1760-1763.
Morlan et al., "Selective depletion of rRNA enables whole transcriptome profiling of archival fixed tissue," PLoS One, Aug. 2012, 7(8):e42882, 8 pages.
Pellestor et al., "The peptide nucleic acids (PNAs), powerful tools for molecular genetics and cytogenetics," Eur J Hum Genet., Sep. 2004, 12(9):694-700.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Aran et al., "xCell: digitally portaying the tissue cellular heterogeneity landscapre," Genome Biol., Nov. 2017, 18(1):220, 14 pages.
Plongthongkum et al., "Advances in the profiling of DNA modifications: cytosine methylation and beyond," Nature Reviews Genetics, Aug. 2014, 15(10):647-661.
Salmén et al., "Barcoded solid-phase RNA capture for Spatial Transcriptomics profiling in mammalian tissue sections," Nature Protocols, Oct. 2018, 13(11):2501-2534.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/000238_VisiumSpatialTissueOptimizationUserGuide_Rev_A. pdf>, 46 pages.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Cruz et al., "Methylation in cell-free DNA for early cancer detection," Ann Oncol., Jun. 2018, 29(6):1351-1353.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Ke et al., "In situ sequencing for RNA analysis in preserved tissue and cells," Nat Methods., Sep. 2013, Supplementary Materials, 29 pages.
Miner et al., "Molecular barcodes detect redundancy and contamination in bairpin-bisulfite PCR," Nucleic Acids Res., Sep. 2004, 32(17):e135, 4 pages.
Wang et al., "Tagmentation-based whole-genome bisulfite sequencing," Nature Protocols, Oct. 2013, 8(10):2022-2032.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Boulé et al., "Terminal deoxynucleotidyl transferase indiscriminately incorporates ribonucleotides and deoxyribonucleotides," J Biol Chem., Aug. 2001, 276(33):31388-93.
Burgess, "Spatial transcriptomics coming of age," Nat Rev Genet., Jun. 2019, 20(6):317, 1 page.
Caliar et al., "A practical guide to hydrogels for cell culture," Nat Methods., Apr. 2016, 13(5):405-14.
Evers et al., "The effect of formaldehyde fixation on RNA: optimization of formaldehyde adduct removal," J Mol Diagn., May 2011, 13(3):282-8.
Gansauge et al., "Single-stranded DNA library preparation from highly degraded DNA using T4 DNA ligase," Nucleic Acids Res., Jun. 2017, 45(10):e79, 10 pages.
Hafner et al., "Identification of microRNAs and other small regulatory RNAs using cDNA library sequencing," Methods, Jan. 2008, 44(1):3-12.
Hanauer et al., "Separation of nanoparticles by gel electrophoresis according to size and shape," Nano Lett, Sep. 2007, 7(9):2881-5.

Ho et al., "Characterization of an ATP-Dependent DNA Ligase Encoded by Chlorella Virus PBCV-1," Journal of Virology, Mar. 1997, 71(3):1931-1937.
Hsuih et al., "Novel, Ligation-Dependent PCR Assay for Detection of Hepatitis C Virus in Serum," Journal of Clinical Microbiology, Mar. 1996, 34(3):501-507.
Hughes et al., "Highly Efficient, Massively-Parallel Single-Cell RNA-Seq Reveals Cellular States and Molecular Features of Human Skin Pathology," bioRxiv, Jul. 2019, 51 pages.
Kumar et al., "Template-directed oligonucleotide strand ligation, covalent intramolecular DNA circularization and catenation using click chemistry," J Am Chem Soc., May 2007, 129(21):6859-64.
Miura et al., "Highly efficient single-stranded DNA ligation technique improves low-input wholegenome bisulfite sequencing by post-bisulfite adaptor tagging," Nucleic Acids Res., Sep. 2019, 47(15):e85, 10 pages.
Mulder et al., "CapTCR-seq: hybrid capture for T-cell receptor repertoire profiling," Blood Advances, Dec. 2018, 2(23):3506-3514.
Nandakumar et al., "RNA Substrate Specificity and Structure-guided Mutational Analysis of Bacteriophage T4 RNA Ligase 2," Journal of Biological Chemistiy, Jul. 2004, 279(30):31337-31347.
Ozsolak et al., "Digital transcriptome profiling from attomole-level RNA samples," Genome Res., Apr. 2010, 20(4):519-25.
Slomovic et al., "Addition of poly (A) and poly(A)-rich tails during RNA degradation in the cytoplasm of human cells," Proc Natl Acad Sci USA, Apr. 2010, 107(16):7407-12.
Ulery et al., "Biomedical Applications of Biodegradable Polymers," J Polym Sci B Polym Phys., Jun. 2011, 49(12):832-864.
Vandenbroucke et al., "Quantification of splice variants using real-time PCR," Nucleic Acids Research, 2001, 29(13):e68, 7 pages.
Zhang et al., "Genome-wide open chromatin regions and their effects on the regulation of silk protein genes in Bombyx mori," Sci Rep., Oct. 2017, 7(1):12919, 9 pages.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Caracausi et al., "Systematic identification of human housekeeping genes possibly useful as references in gene expression studies," Molecular Medicine Reports, Jul. 6, 2017, 16:2397-2410.
Dheda et al., "Validation of housekeeping genes for normalizing RNA expression in real-time PCR," Biotechniques, Jun. 6, 2018, 37(1):112-119.
Dundas et al., "Reference genes for measuring mRNA expression," Theory Biosci., May 17, 2012, 131:215-223.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Luo et al., "Probing infectious disease by single-cell RNA sequencing: Progresses and perspectives," Computational and Structural Biotechnology Journal, Oct. 21, 2020, 18:2962-2971.
Ma et al., "Isothermal amplification method for next-generation sequencing," PNAS, Aug. 12, 2013, 110(35):14320-14323.
O'Huallachain et al., "Ultra-high throughput single-cell analysis of proteins and RNAs by split-pool synthesis," Communications Biology, 2020, 3:213, 19 pages.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Satija et al., "Spatial reconstruction of single-cell gene expression data," Nature, Apr. 13, 2015, 33(5):495-402, 14 pages.
Stoeckius et al., "Simultaneous epitope and transcriptome measurement in single cells," Nature Methods, Jul. 31, 2017, 14(9):865-868.
Zahra et al., "Assessment of Different Permeabilization Methods of Minimizing Damage to the Adherent Cells for Detection of Intracel-

(56) References Cited

OTHER PUBLICATIONS lular RNA by Flow Cytometry," Avicenna Journal of Medical Biotechnology, Jan. 1, 2014, 6(1):38-46.
Adam et al., "Psychrophilic proteases dramatically reduce single-cell RNA-seq artifacts: a molecular atlas of kidney development," Development, Oct. 1, 2017, 144(19):3625-3632.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Eastburn et al., "Identification of Genetic Analysis of Cancer Cells with PCT-activated Cell Sorting," Nucleic Acids Research, Jul. 16, 2014, 42(16):e128, 10 pages.
Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.
Edsgard et al., "Identification of spatial expression trends in single-cell gene expression data," Nature Methods, Mar. 19, 2018, 15: 339-342, 16 pages.
Fan et al., "A versatile assay for high-throughput gene expression profiling on universal array matrices," Genome Research, May 1, 2004, 14(5):878-885.
Ha et al, "Self-assembly hollow nanosphere for enzyme encapsulation," Soft Matter, Feb. 11, 2010, 6, 1405-1408, 10 pages.
Hu et al., "A thermo-degradable hydrogel with light-tunable degradation and dreg release," Biomaterials, Jan. 2017, 112:133-140.
Ju et al, "Supramolecular dendrimer capsules by cooperative binding," Chem. Commun., Jan. 7, 2011, 47(1):268-270, 8 pages.
Kuiper et al, "Enzymes containing porous polymersomes as nano reaction vessels for cascade reactions," Org. Biomol, Chem, Oct. 15, 2008, 6(23):4315-4318.
Liu et al., "Preparation and Characterization of Temperature-Sensitive Poly(N-isopropylacrylamide)-b-poly(d,l-lactide) Microspheres for Protein Delivery," Biomacromolecules, 2003, 4(6):1784-1793.
Lyu et al., "One-Pot Synthesis of Protein-Embedded Metal-Organic Frameworks with Enhanced Biological Activities," Nano Lett., Sep. 11, 2014, 14:5761-5765.
Massoni-Badosa et al, "Sampling artifacts in single-cell genomics cohort studies," bioRxiv, Jan. 15, 2020, 32 pages.
Miller et al., "Rapid and Efficient Enzyme Encapsulation in a Dendrimer Silica Nanocomposite," Macromolecular Bioscience, Oct. 25, 2006, 6(10):839-845.
O'Flanagan et al, "Dissociation of solid tumor tissues with cold active protease for single-cell RNA-seq minimizes conserved collagenase-associated stress responses," Genome Biology, Oct. 17, 2019, 20:210, 13 pages.
Pellegrino et al., "High-throughput Single-cell DNA Sequencing of Acut Myeloid Leukemia Tumors with Droplet Microfluidics," Genome Research, Aug. 7, 2018, 28(9):1345-1352.
Rahimi et al, "Synthesis and Characterization of Thermo-Sensitive Nanoparticles for Drug Delivery Applications," J. Biomed. Nanotechnol. Dec. 2008, 4(4):482-490, 19 pages.
Shieh, et al., "Imparting Functionality to Biocatalysts via Embedding Enzymes into Nanoporous Materials by a de Novo Approach: Size-Selective Sheltering of Catalase in Metal-Organic Framework Microcrystals," J Am Chem Soc., Apr. 8, 2015, 137(13):4276-4279, 4 pages.
Soderberg, "Droplet Microfluidics Reverse Transcription and PCR Towards Single Cell and Exosome Analysis," Doctoral Thesis, KTH School of Biotechnology Science for Life Laboratory, 2017, 69 pages.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.

\* cited by examiner

SPATIAL ASSAYS WITH PERTURBED CELLS

CROSS-REFERENCE TO RELATED APPLICATIONS

This application claims priority to U.S. Provisional Patent Application No. 62/963,897, filed Jan. 21, 2020; and U.S. Provisional Patent Application No. 62/963,879, filed Jan. 21, 2020. The contents of each of these applications are incorporated herein by reference in their entireties.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Genetic material, and related gene and protein expression, influences cellular fate and behavior. Screens such as those based on CRISPR can help elucidate gene function.

However, current methods have inherent limitations, and it remains difficult to assay complex phenotypes including transcriptional profiles.

SUMMARY

This disclosure relates to methods for spatial profiling at least one biological analyte present in a cell comprising a small molecule.

In one aspect provided herein is a method for spatial profiling a biological analyte in a cell comprising: (a) contacting the cell with a substrate comprising a plurality of capture probes, wherein a capture probe of the plurality comprises a first barcode and a capture domain, and wherein the cell comprises a small molecule and a second barcode; (b) releasing the biological analyte from the cell, wherein the biological analyte is bound by the capture probe at a distinct spatial position of the substrate; (c) detecting the biological analyte bound by the capture probe; and (e) correlating the biological analyte with the first barcode and the second barcode at the distinct spatial position of the substrate, thus profiling the biological analyte as present in the cell at the distinct spatial position. In some embodiments, the small molecule and second barcode are introduced into the cell using a particle.

In some instances, disclosed herein is a method for determining the presence or abundance of a moiety in a cell comprising: (a) contacting the cell with an array comprising a plurality of capture probes, wherein a capture probe of the plurality of capture probes comprises: (i) a spatial barcode and (ii) a capture domain, wherein the cell comprises the moiety and wherein the moiety comprises a moiety sequence; (b) hybridizing a moiety sequence to the capture domain; and (c) determining (i) all or a part of the sequence of the moiety sequence bound to the capture domain, or a complement thereof, and (ii) all or a part of the sequence of the spatial barcode, or a complement thereof, and using the determined sequence of (i) and (ii) to determine the presence or abundance of the moiety in the cell.

Also provided herein is a method for spatial profiling a biological analyte in a cell comprising: (a) contacting a plurality of cells with a plurality of particles, wherein a particle of the plurality of particles comprises a small molecule and a second barcode, and wherein the cell uptakes the small molecule and the second barcode; (b) contacting the cell with a substrate comprising a plurality of capture probes, wherein a capture probe of the plurality comprises a first barcode and a capture domain; (c) releasing the biological analyte from the cell, wherein the biological analyte is bound by the capture probe at a distinct spatial position of the substrate; (d) detecting the biological analyte bound by the capture probe; and (e) correlating the biological analyte with the first barcode and the second barcode at the distinct spatial position of the substrate, thus profiling the biological analyte as present in the cell at the distinct spatial position.

In some instances, the method further comprises: (a) hybridizing an analyte to a second capture domain of a second probe, wherein the second probe comprises a second spatial barcode and the second capture domain, and wherein the second capture probe is in proximity to the capture probe that is hybridized to the moiety sequence; and (b) determining (i) all or a part of a sequence of an analyte bound to the second capture domain, or a complement thereof, and (ii) all or a part of the sequence of the second spatial barcode, or a complement thereof, and using the determined sequence of (i) and (ii) to determine the abundance of the analyte in the cell.

In some instances, the moiety sequence is substantially complementary to the capture domain, optionally wherein the moiety sequence is a polyadenylated sequence. In some instances, the moiety further comprises a particle introduced into the cell, wherein the particle comprises a small molecule and the moiety sequence. In some instances, the cell is from a plurality of cells, and wherein the plurality of cells is contacted with a plurality of particles, and wherein the cell uptakes the particle.

In some embodiments, the particle is a nanoparticle. In some embodiments, the particle comprises gold, silica, polyethylene glycol (PEG)-poly(lactide), 1,2-distearoyl-sn-glycero-3-phosphoethanolamine-PE2000, silver, cadmium-selenide, poly(methylacrylic) acid, 1,2-distearoyl-sn-glycero-3-phosphocholine (DSPC)-cholesterol-1,2-distearoyl-sn-glycero-3-phosphocholine (POPG), poly(lactic-co-glycolic acid) (PLGA)-polyethylene glycol, or a combination thereof.

In some embodiments, the particle comprises a surface modification. In some embodiments, the surface modification comprises cysteine-cyan5, a cationic monolayer, a nucleic acid, poly(isobutylene-alt-maleic anhydride), a coating with fetal bovine serum (FBS), citrate, 5-aminovaleric acid, L-DOPA, melatonin, serotonin-HCl, MUS/OT, glutathione/glucose, polyethyleneimine, or a combination thereof.

In some embodiments, the small molecule binds to a biological target. In some embodiments, the biological target is a protein or a nucleic acid. In some embodiments, the protein is a kinase, a receptor, a channel, an enzyme, or a combination thereof. In some embodiments, the protein is a G protein-coupled receptor, a kinase, a protease, an esterase, a phosphatase, ligand-gated ion channel, a voltage-gated ion channel, or a nuclear receptor.

In some embodiments, the small molecule inhibits the biological target. In some embodiments, the small molecule activates the biological target. In some embodiments, the cell is a mammalian cell.

In one aspect, provided herein is a method for spatial profiling a biological analyte present in a genetically-perturbed cell comprising: (a) contacting the genetically-perturbed cell with a substrate comprising a plurality of capture probes, wherein a capture probe of the plurality comprises a first barcode and a capture domain; (b) releasing the biological analyte from the genetically-perturbed cell, wherein the biological analyte is bound by a capture probe at a distinct spatial position of the substrate; (c) detecting the biological analyte bound by the capture probe; and (e) correlating the biological analyte with the first barcode from the capture probe at the distinct spatial position of the substrate; thus profiling the biological analyte as present in the genetically-perturbed cell at the distinct spatial position.

In some embodiments, the genetically-perturbed cell comprises a clustered regularly interspaced short palindromic repeats (CRISPR)-based genetic perturbation. In some embodiments, the genetically-perturbed cell comprises a second barcode that identifies the genetic perturbation of the cell.

In some embodiments, the step of correlating the biological analyte with the first barcode of the capture probe at the distinct spatial position of the substrate further comprises correlating the genetic perturbation of the cell to a distinct spatial position of the substrate using the second barcode that identifies the genetic perturbation of the cell.

In some embodiments, the genetically-perturbed cell comprises a polyadenylated nucleotide sequence that identifies the genetic perturbation. In some embodiments, the step of correlating the biological analyte with the first barcode of the capture probe at the distinct spatial position of the substrate further comprises correlating the genetic perturbation of the cell to a distinct spatial position of the substrate using the polyadenylated nucleotide sequence.

Also provided herein is a method for spatial profiling a biological analyte present in a genetically-perturbed cell comprising: (a) transducing a cell with a vector to form the genetically-perturbed cell; (b) contacting the genetically-perturbed cell with a substrate comprising a plurality of capture probes, wherein a capture probe of the plurality of capture probes comprises a first barcode and a capture domain; (c) releasing the biological analyte from the genetically-perturbed cell, wherein the biological analyte is bound by the capture probe at a distinct spatial position of the substrate; (e) detecting the biological analyte bound by the capture probe; and (f) correlating the biological analyte with the first barcode of the capture probe at the distinct spatial position of the substrate, thus profiling the biological analyte as present in the genetically-perturbed cell at the distinct spatial position.

In some embodiments, the vector is a lentiviral vector. In some embodiments, the lentiviral vector is a CRISPR lentiviral vector. In some embodiments, the CRISPR lentiviral vector comprises a guide RNA (gRNA).

In some embodiments, the CRISPR lentiviral vector comprises a second barcode identifying the gRNA. In some embodiments, the gRNA is a single guide RNA (sgRNA). In some embodiments, the step of correlating the biological analyte with the first barcode of the capture probe at the distinct spatial position of the substrate further comprises correlating the genetic perturbation to a distinct spatial position of the substrate using a second barcode that identifies the genetic perturbation.

In some embodiments, the vector comprises a polyadenylated or an oligo (dT) nucleotide sequence. In some embodiments, correlating the biological analyte with the first barcode of the capture probe at the distinct spatial position of the substrate further comprises correlating the genetic perturbation to the distinct spatial position of the substrate using the polyadenylated or the oligo (dT) nucleotide sequence. In some embodiments, the genetically-perturbed cell is a mammalian cell.

In some embodiments, the step of releasing the biological analyte comprises permeabilizing the cell. In some embodiments, the method further comprises fixing the cell prior to the permeabilizing the cell. In some embodiments, the method further comprises staining the cell prior to the permeabilizing the cell. In some embodiments, the cell is stained after the fixing the cell. In some embodiments, the cell is fixed and permeabilized prior to releasing the biological analyte from the biological sample. In some embodiments, the permeabilizing the cell comprises electrophoresis. In some embodiments, the permeabilizing the cell comprises administering a permeabilization reagent.

In some embodiments, the step of releasing the biological analyte comprises permeabilizing the genetically-perturbed cell. In some embodiments, the method further comprises fixing the genetically-perturbed cell prior to permeabilizing the genetically-perturbed cell. In some embodiments, the method further comprises staining the genetically-perturbed cell prior to permeabilizing the genetically-perturbed cell. In some embodiments, the genetically-perturbed cell is stained after the genetically-perturbed cell is fixed. In some embodiments, the genetically-perturbed cell is fixed and permeabilized prior to the step of releasing the biological analyte from the biological sample.

In some embodiments, the step of permeabilizing comprises electrophoresis. In some embodiments, the step of permeabilizing comprises administering a permeabilization reagent.

In some embodiments, the method further comprises imaging the genetically-perturbed cell. In some embodiments, the imaging is performed prior to releasing the biological analyte from the genetically-perturbed cell. In some embodiments, the imaging is performed after releasing the biological analyte from the genetically-perturbed cell. In some embodiments, the imaging is used to determine the morphology of the genetically-perturbed cell.

In some instances, the cell is a mammalian cell. In some instances, the cell is permeabilized prior to hybridizing the analyte to the capture domain. In some instances, the methods further include staining the cell prior to permeabilizing the cell.

In some embodiments, the method further comprises imaging the cell. In some embodiments, the imaging is performed prior to releasing the biological analyte from the cell. In some embodiments, the imaging is performed after releasing the biological analyte from the cell. In some embodiments, the imaging is used to determine the morphology of the cell.

In some embodiments, the capture probe comprises a unique molecular identifier. In some embodiments, the capture probe comprises a cleavage domain. In some embodiments, the capture probe comprises a functional domain. In some embodiments, the functional domain is a primer sequence. In some embodiments, the capture probe comprises a capture domain. In some embodiments, the capture domain comprises a poly-dT sequence. In some embodiments, the capture domain is configured to hybridize to a poly-A tail of an mRNA.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

BRIEF DESCRIPTION OF THE DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
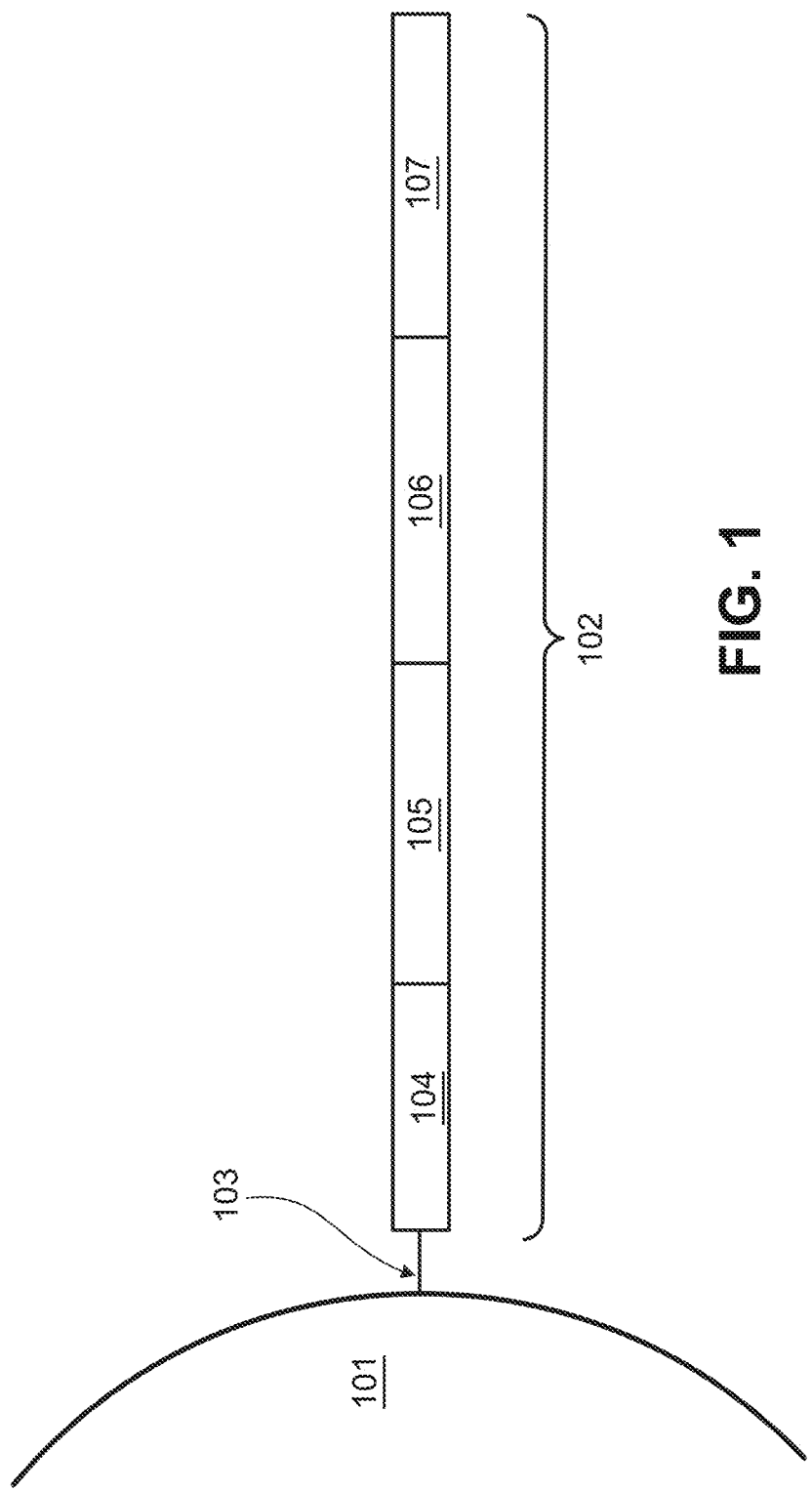
FIG. 1 is a schematic diagram showing an example of a barcoded capture probe, as described herein.

Pooled screens have the potential to exponentially improve throughput and reduce overall costs dramatically due to the massive parallelization achieved through pooling. However, most pooling strategies to date have primarily focused on pooled screens involving nucleic acids (e.g., gRNA or plasmids). Moreover, methods to perform pooled genetic perturbation screens with morphometric phenotypic readouts combining spatial information with sequencing do not exist. A pooled screening approach with morphometric readout and spatial analysis using barcoded arrays offers a significant improvement in overall throughput and cost of performing pooled small molecule perturbation screens as well as pooled genetic perturbation screens. Thus, provided herein are methods for profiling a biological analyte, e.g., any of the analytes described herein, in a cell including a moiety (e.g., a small molecule and/or a genetic perturbation introduced into the cell). Also provided herein are methods for determining the abundance of a moiety, e.g., any of the moieties described herein, in a cell. Also provided herein are methods for determining the location of a biological analyte, e.g., any of the analytes as described herein, and/or a moiety, e.g., any of the moieties described herein, in a biological sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises an additional functional sequence that can be located, e.g., between spatial barcode 105 and UMI sequence 106, between UMI sequence 106 and capture domain 107, or following capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
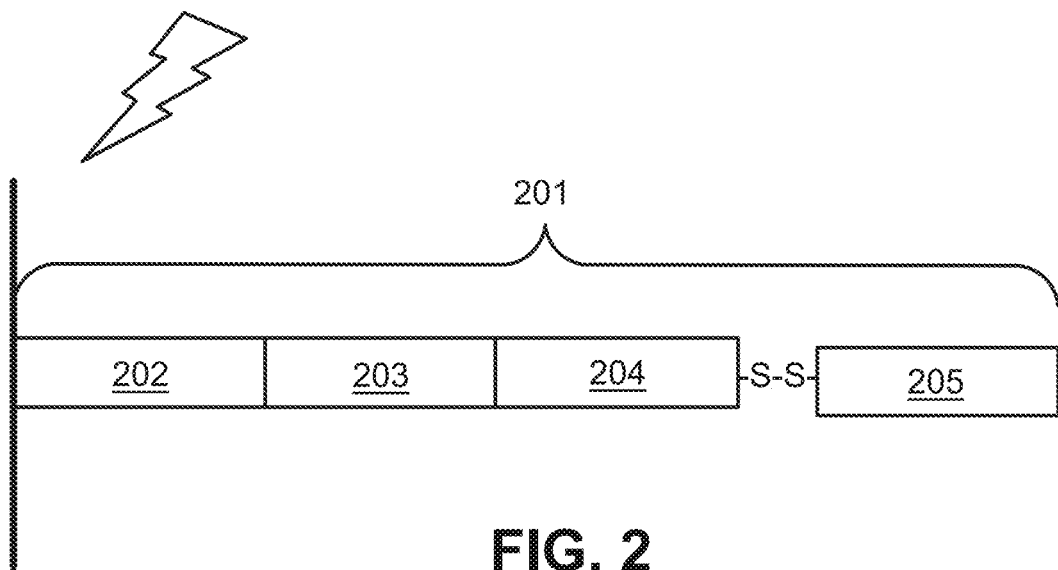
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
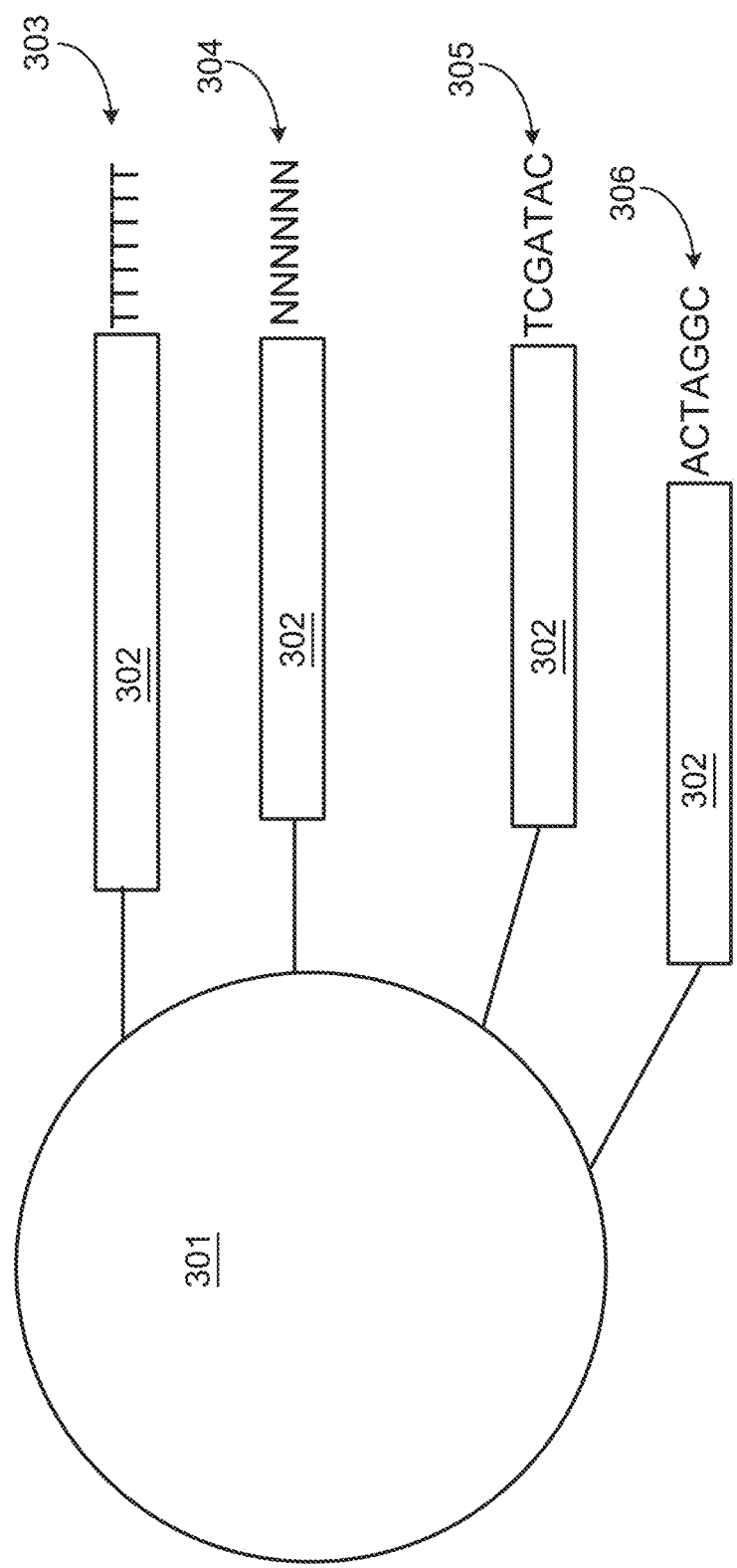
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent.

Figure 4:
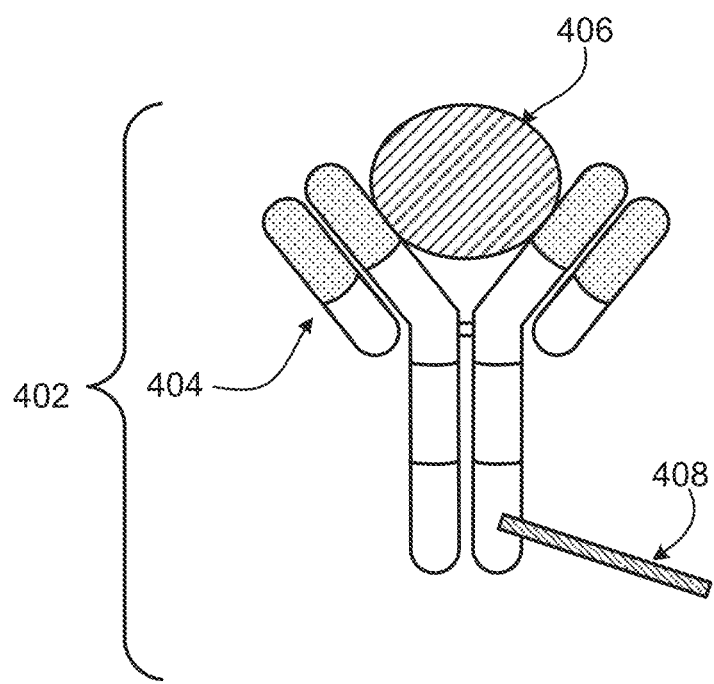
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
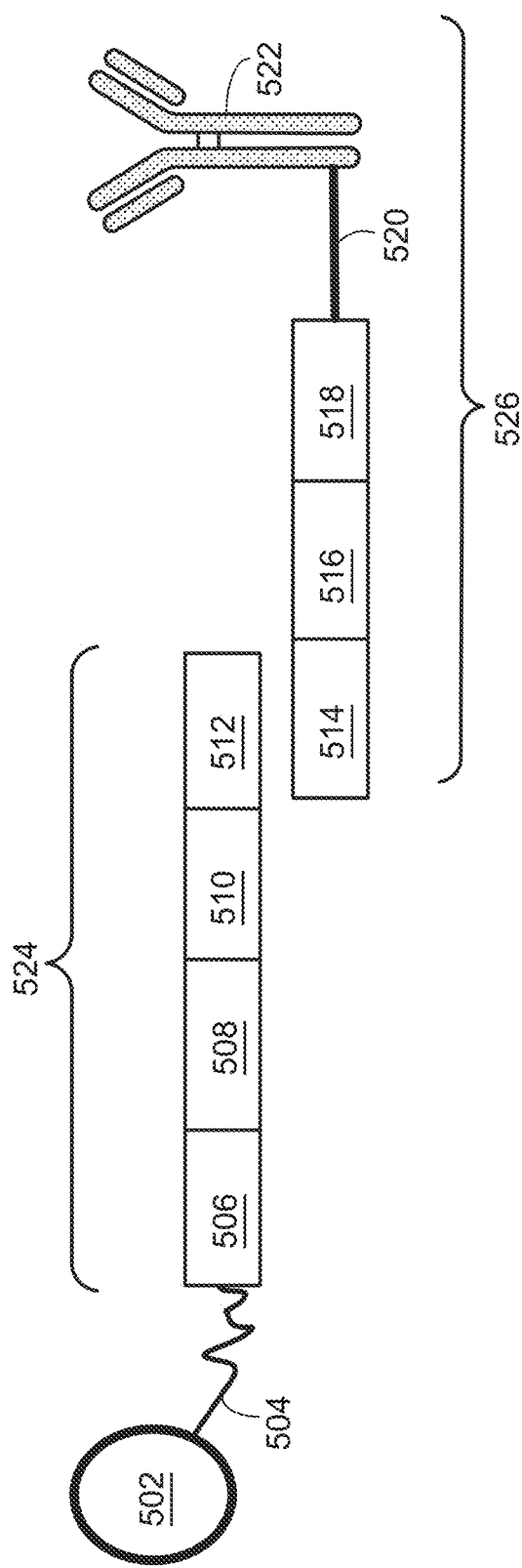
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
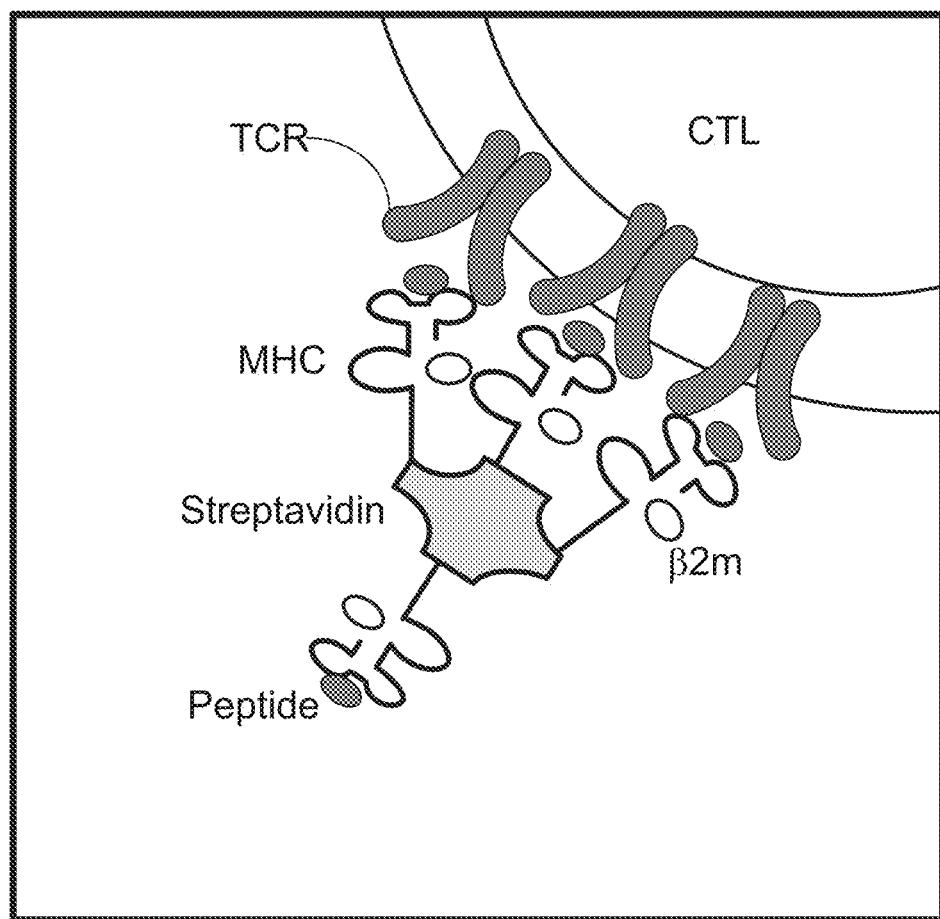
FIGS. 6A, 6B, and 6C are schematics illustrating how streptavidin cell tags can be utilized in an array-based system to produce a spatially-barcoded cells or cellular contents.
Figure 6B:
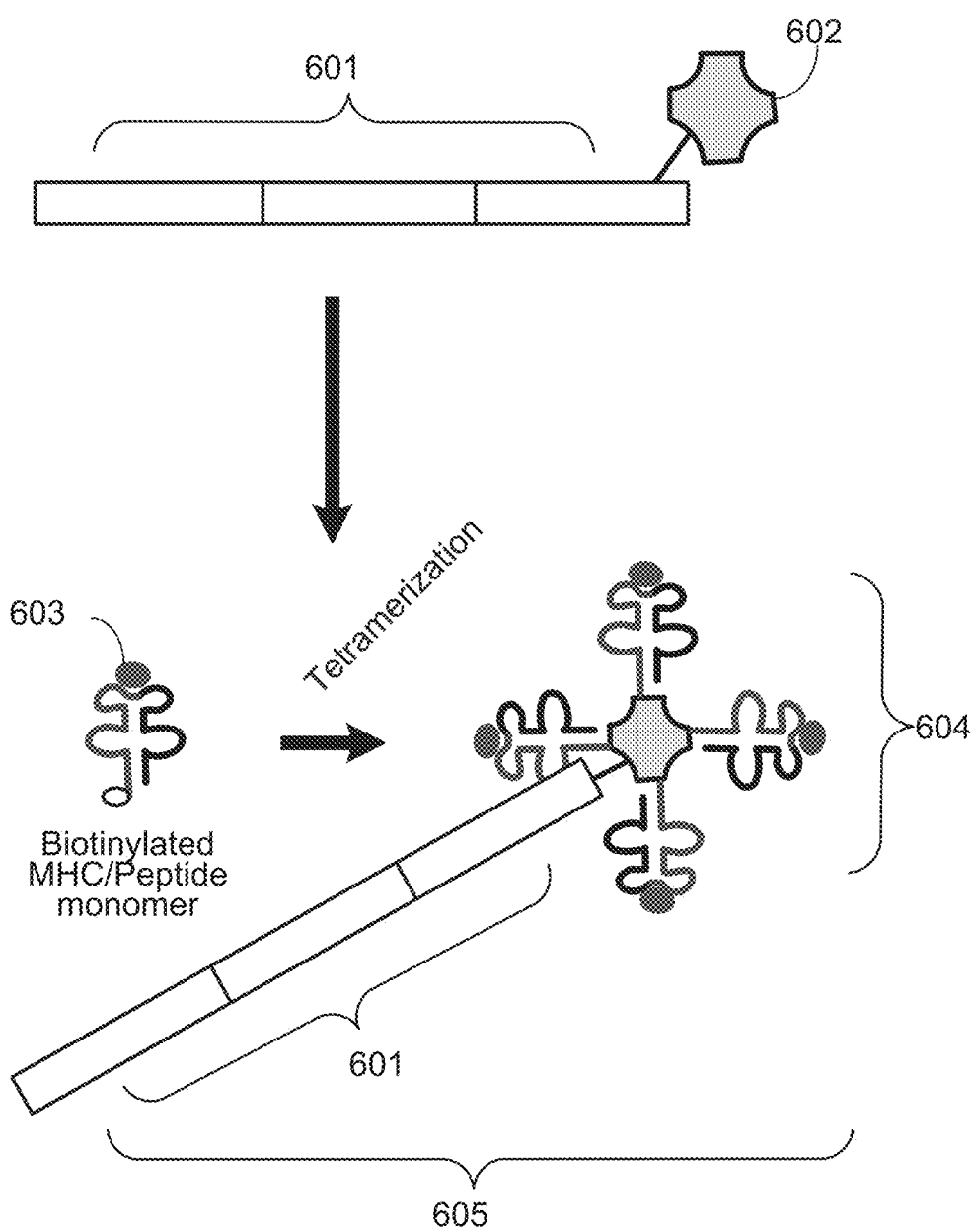
Figure 6C:
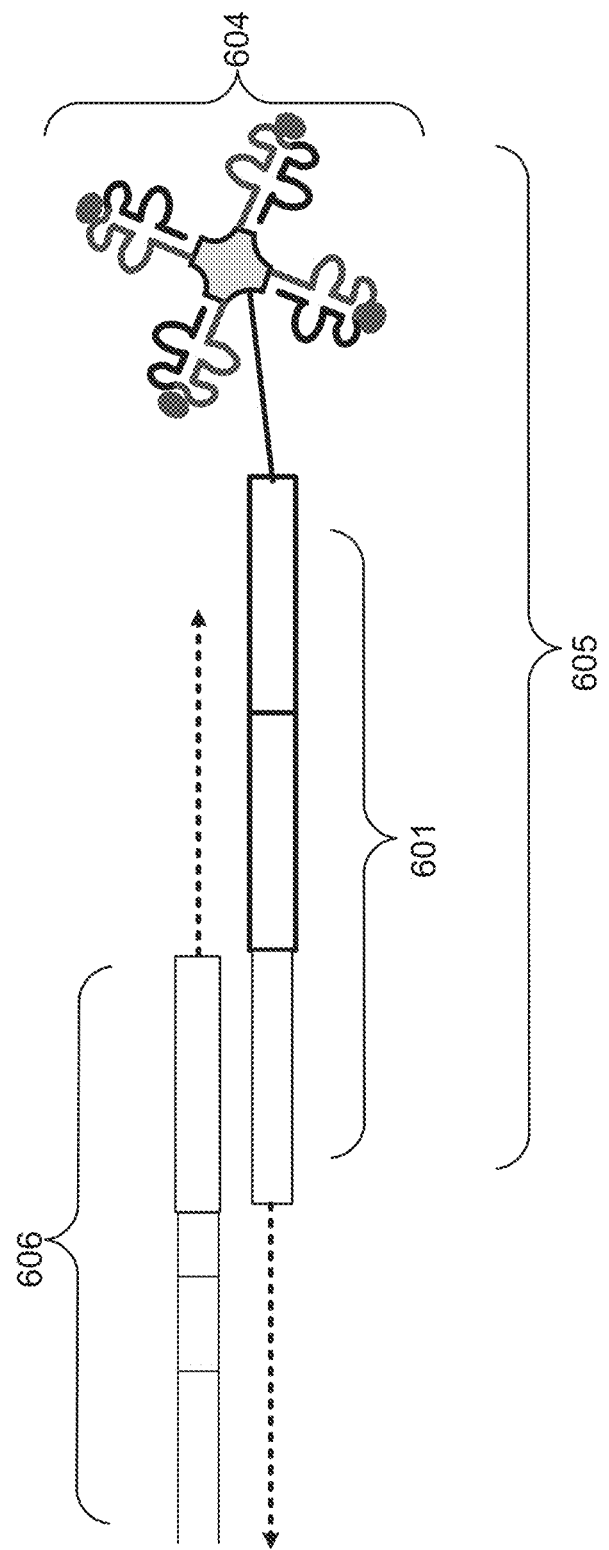

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 1105. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

Figure 7:
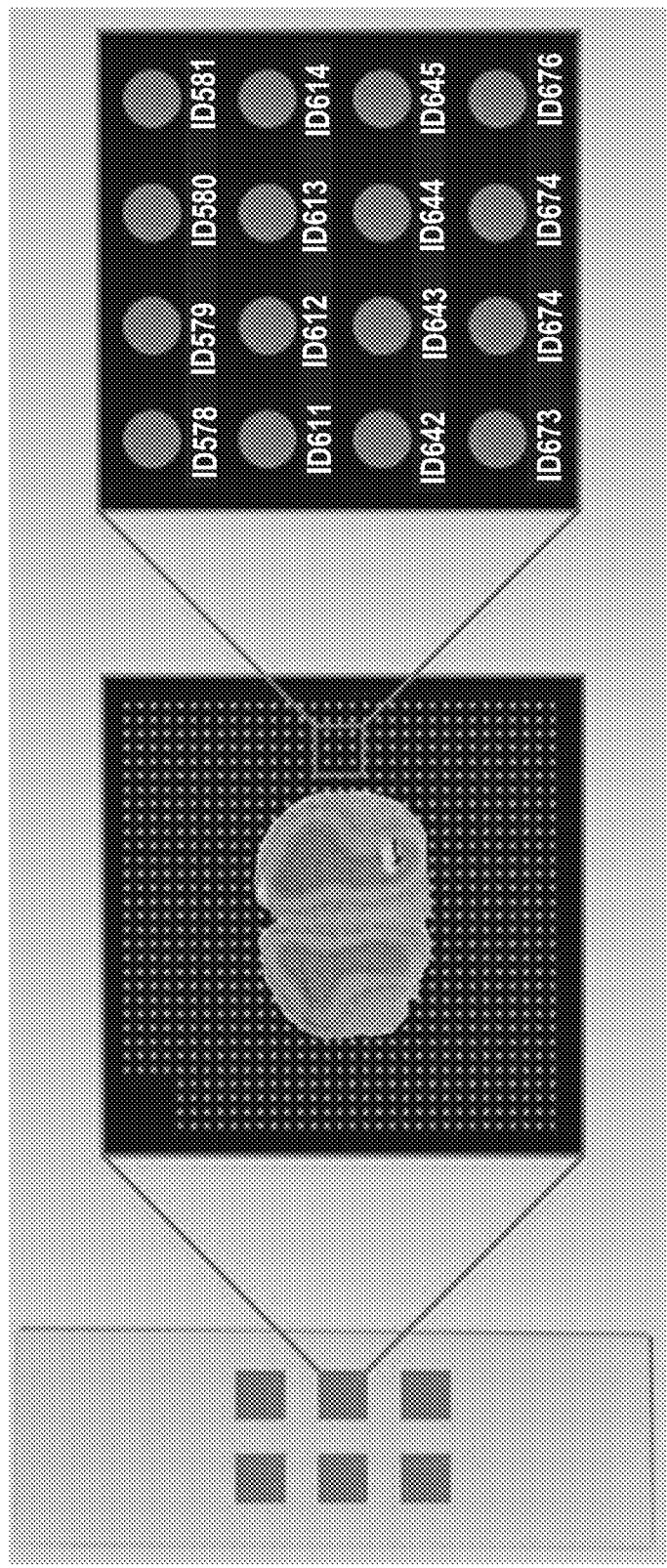
FIG. 7 is a schematic showing the arrangement of barcoded features within an array.

FIG. 7 depicts an exemplary arrangement of barcoded features within an array. From left to right, FIG. 7 shows (left) a slide including six spatially-barcoded arrays, (center) an enlarged schematic of one of the six spatially-barcoded arrays, showing a grid of barcoded features in relation to a biological sample, and (right) an enlarged schematic of one section of an array, showing the specific identification of multiple features within the array (labelled as ID578, ID579, ID560, etc.).

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

I. Spatial Analytical Methodology and Perturbation of Cells
  (a) Introduction

A pooled screening approach that utilizes a morphometric readout and spatial analysis offers significant improvements for pooled perturbation screens. In such screens, a biological sample or a cell, e.g., a cell in a biological sample, can be perturbed by a perturbation agent. As described herein, a "perturbation agent" or "perturbation reagent" or "moiety" can be a small molecule, an antibody, a drug, an aptamer, a nucleic acid (e.g., miRNA), a CRISPR crRNA/sgRNA, TALEN, zinc finger nuclease, antisense oligonucleotide a physical environmental (e.g., temperature change), and/or any other known perturbation agents where the agent alters equilibrium or homeostasis. After perturbation of the biological sample or cell, e.g., a cell in a biological sample, the biological sample or cell comprising a moiety can be (i) imaged; and/or (ii) contacted with a spatial array to allow for profiling a biological analyte and/or determining the identity of the moiety in a cell at a distinct location within a biological sample. Such methods can be useful for determining the abundance of a biological analyte in a cell comprising a moiety at a distinct spatial position on a substrate. These methods can also be useful, for example, for detecting a perturbation (e.g., a change in a biological analyte such as a change in the amount of the biological analyte) in a cell comprising a moiety (e.g., a small molecule or genetic perturbation) compared to a cell comprising a different moiety or a cell not comprising a moiety.

Accordingly, provided herein are methods for determining the presence or abundance of a moiety in a cell comprising: (a) contacting the cell with an array comprising a plurality of capture probes, wherein a capture probe of the plurality of capture probes comprises: (i) a spatial barcode and (ii) a capture domain, wherein the cell comprises the moiety and wherein the moiety comprises a moiety sequence; (b) hybridizing a moiety sequence to the capture domain; and (c) determining (i) all or a part of the sequence of the moiety sequence bound to the capture domain, or a complement thereof, and (ii) all or a part of the sequence of the spatial barcode, or a complement thereof, and using the determined sequence of (i) and (ii) to determine the abundance of the moiety in the cell. In some embodiments, the method further includes determining (i) all or a part of a sequence of an analyte bound to a capture domain, or a complement thereof, and (ii) all or a part of the sequence of the spatial barcode, or a complement thereof, and using the determined sequence of (i) and (ii) to determine the abundance of the analyte in the cell.

In some embodiments, provided herein are methods for determining an abundance of an analyte or moiety in a cell comprising: (a) contacting the cell with an array comprising a plurality of capture probes, wherein a capture probe of the plurality of capture probes comprises: (i) a spatial barcode and (ii) a capture domain; wherein the cell comprises the moiety and wherein the moiety comprises a moiety sequence; (b) hybridizing the analyte or the moiety sequence to the capture domain; and (c) determining (i) all or a part of the sequence of the analyte or the moiety sequence bound to the capture domain, or a complement thereof, and (ii) all or a part of the sequence of the spatial barcode, or a complement thereof, and using the determined sequence of (i) and (ii) to determine the abundance of the analyte or the moiety in the cell. A "moiety sequence" as used herein refers to a sequence that can be used to identify a moiety. For example, a moiety sequence can be unique to each moiety (e.g., each small molecule or each genetic perturbation).

In some embodiments, the methods provided herein include profiling a biological analyte, e.g., any of the analytes as described herein, in a cell including a moiety (e.g., a small molecule and/or genetic perturbation introduced into the cell). Also provided herein are methods for determining the abundance of a moiety, e.g., any of the moieties described herein, in a cell. In some embodiments, the cell is a member of a plurality of cells, e.g., the cell is in a biological sample. In some embodiments, the methods provided herein include determining the location of a biological analyte, e.g., any of the analytes as described herein, and/or a moiety, e.g., any of the moieties described herein, in a biological sample. In some instances, both the abundance and the location of a biological analyte and/or a moiety are determined.

Also provided herein are methods for profiling a biological analyte, e.g., any of the analytes as described herein, in a cell including a small molecule (e.g., a small molecule introduced into the cell). In some embodiments, the methods described herein can include releasing a biological analyte from a cell including a small molecule (e.g., a small molecule introduced into the cell). The released biological analyte can be bound by a capture probe as described herein at a distinct spatial position on a substrate and detected. The bound biological analyte can then be correlated with a barcode of the capture probe at a distinct spatial position of the substrate.

Also provided herein is a method for spatial profiling a biological analyte in a cell including: contacting a plurality of cells with a plurality of particles, wherein a particle of the plurality of particles includes a small molecule and a second barcode, and wherein the cell uptakes the small molecule and the second barcode; contacting the cell with a substrate including a plurality of capture probes, wherein a capture probe of the plurality includes a first barcode and a capture domain; releasing the biological analyte from the cell, wherein the biological analyte is bound by the capture probe at a distinct spatial position of the substrate; detecting the biological analyte bound by the capture probe; and correlating the biological analyte with the first barcode and the second barcode at the distinct spatial position of the substrate, thus profiling the biological analyte as present in the cell at the distinct spatial position.

In some embodiments, a method for spatial profiling a biological analyte in a cell includes: contacting the cell with a substrate including a plurality of capture probes, wherein a capture probe of the plurality includes a first barcode and a capture domain, and wherein the cell includes a small molecule and a second barcode; releasing the biological analyte from the cell, wherein the biological analyte is bound by the capture probe at a distinct spatial position of the substrate; detecting the biological analyte bound by the capture probe; and correlating the biological analyte with the first barcode and the second barcode at the distinct spatial position of the substrate, thus profiling the biological analyte as present in the cell at the distinct spatial position.

In some embodiments, the methods described herein can include releasing a biological analyte from a genetically-perturbed cell. The released biological analyte can be bound by a capture probe as described herein at a distinct spatial position on a substrate and detected. The bound biological analyte can then be correlated with a barcode of the capture probe at a distinct spatial position of the substrate. Such methods can be useful for correlating a genetic perturbation of a cell to a biological analyte at a distinct spatial position on a substrate.

Also provided herein are methods for spatial profiling a biological analyte present in a genetically-perturbed cell that include transducing a cell with a vector to form the genetically-perturbed cell; contacting the genetically-perturbed cell with a substrate including a plurality of capture probes, wherein a capture probe of the plurality of capture probes includes a first barcode and a capture domain; releasing the biological analyte from the genetically-perturbed cell, wherein the biological analyte is bound by the capture probe at a distinct spatial position of the substrate; detecting the biological analyte bound by the capture probe; and correlating the biological analyte with the first barcode of the capture probe at the distinct spatial position of the substrate, thus profiling the biological analyte as present in the genetically-perturbed cell at the distinct spatial position.

In some embodiments, a method for spatially profiling a biological analyte present in a genetically-perturbed cell includes contacting the genetically-perturbed cell with a substrate including a plurality of capture probes, wherein a capture probe of the plurality includes a first barcode and a capture domain; releasing the biological analyte from the genetically-perturbed cell, wherein the biological analyte is bound by a capture probe at a distinct spatial position of the substrate; detecting the biological analyte bound by the capture probe; and correlating the biological analyte with the first barcode from the capture probe at the distinct spatial position of the substrate; thus profiling the biological analyte as present in the genetically-perturbed cell at the distinct spatial position.

(b) Generation of Libraries

1. Generating Pooled Small Molecule Libraries

In some embodiments, disclosed herein are methods of generating a small molecule library. Methods of generating a small molecule library have been described, for example, in U.S. Pat. Nos. 8,951,728; 6,677,160; Dandapani et al. *Curr Protoc Chem Biol.* 4:177-191, 2012; Hajduk et al. *Nature.* 470:42-43, 2011; Paricharak et al. *Briefings in Bioinformatics.* 19(2):277-285, 2018; and Harris et al. *Comb Chem High Throughput Screen.* 14(6):521-531, 2011; each of which is incorporated herein by reference in its entirety. Generating a barcoded small molecule library can include loading a plurality of particles with a plurality of small molecules and a plurality of moiety sequences (e.g., a second barcode). In some embodiments, a moiety sequence (e.g., a second barcode) is affixed to each small molecule.

Methods of introducing a small molecule into a cell are known to one of skill in art. Such methods include using particles (e.g., nanoparticles) to introduce the small molecule into the cell. Accordingly, in some embodiments, a moiety as described herein further comprises a particle introduced into the cell. In some embodiments, the particle is taken up by the cell through diffusion, electroporation, receptor-mediated endocytosis, or a combination thereof. See, e.g., Behzadi et al., *Chem Soc Rev.* 46(14): 4218-4244, 2017; Mosquera et al., *Acc Chem Res,* 51(9):2305-2313, 2018; Jahangirian et al., *Int J Nanomedicine,* 14:1633-1657, 2019; and Zhao, *Scientific Reports.* 7:4131, 2017; each of which is incorporated herein by reference in its entirety. In some embodiments, the cell is from a plurality of cells, and the plurality of cells is contacted with a plurality of particles, and a cell uptakes the particle. In some embodiments, the particle includes a moiety sequence. In some embodiments, the moiety sequence is substantially complementary to the capture domain. In some embodiments, the moiety sequence is a polyadenylated sequence.

In some embodiments, the small molecule library includes small molecules with validated biological and pharmacological activities with particular solubility, purity, and stability of the compounds. In some embodiments, the library is fully randomized, with no sequence preferences or constants at any position. In another embodiment, the library is biased.

In some embodiments, the small molecule binds to a biological target. In some embodiments, the biological target is a protein or a nucleic acid. In some embodiments, the protein is a kinase, a receptor, a channel, an enzyme, or a combination thereof. In some embodiments, the protein is a G protein-coupled receptor, a kinase, a protease, an esterase, a phosphatase, ligand-gated ion channel, a voltage-gated ion channel, or a nuclear receptor. In some embodiments, the small molecule interacts with a known cellular molecule or known classes of cellular molecules. In some embodiments, the small molecules include but are not limited to inhibitors, antagonists, and agonists of various cellular pathways, including for example, pathways involving DNA damage/DNA repair, cell cycle/checkpoints, JAK/STAT signaling, MAPK signaling, GPCR/G protein, angiogenesis, immunology and inflammation, endocrinology and hormones, cancer, metabolism, and stem cells. In some embodiments, the small molecule inhibits the biological target. In some embodiments, the small molecule activates the biological target. In some embodiments, correlating the biological analyte with the first barcode and the second barcode at the distinct spatial position of the substrate, thus profiling the biological analyte as present in the cell at the distinct spatial position.

In some embodiments, one or more small molecules are encapsulated into one or more particles. In some embodiments, one or more small molecules and one or more moiety sequences (e.g., second barcodes) are encapsulated into one or more particles. In some embodiments, one or more small molecules are loaded onto one or more particles. Any particle that can introduce a small molecule into a cell can be used. Such particles can include, for example, gold, silica, polyethylene glycol (PEG)-poly(lactide), silver, cadmium-selenide, poly(methylacrylic) acid, a lipid (e.g., 2-distearoyl-sn-glycero-3-phosphocholine (DSPC)-cholesterol-1,2-distearoyl-sn-glycero-3-phosphocholine (POPG) and poly (lactic-co-glycolic acid) (PLGA)-polyethylene glycol), polystyrene, carboxylated polystyrene, $NH_2$-labeled polystyrene, polystyrene latex, fullerene, alginate-chitosan, a polymer-lipid hybrid (e.g., 1,2-distearoyl-sn-glycero-3-phosphoethanolamine-PE2000), a quantum dot, and any combination thereof.

In some embodiments, a particle described herein can be spherical or disc-shaped. In some embodiments, the diameter of the particle is about 1 nm to about 2500 nm. For example, about 1 nm to about 200 nm, about 1 nm to about 400 nm, about 1 nm to about 600 nm, about 1 nm to about 800 nm, about 1 nm to about 1000 nm, about 1 nm to about 1200 nm, about 1 nm to about 1400 nm, about 1 nm to about 1600 nm, about 1 nm to about 1800 nm, about 1 nm to about 2000 nm, about 1 nm to about 2200 nm, about 1 nm to about 2400 nm, about 2300 nm to about 2500 nm, about 2100 nm to about 2500 nm, about 1900 nm to about 2500 nm, about 1700 nm to about 2500 nm, about 1500 nm to about 2500 nm, about 1300 nm to about 2500 nm, about 1100 nm to about 2500 nm, about 900 nm to about 2500 nm, about 700 nm to about 2500 nm, about 500 nm to about 2500 nm, about 300 nm to about 2500 nm, or about 100 nm to about 2500 nm. In some embodiments, the diameter of the particle is about 5 nm to about 500 nm. For example, about 5 nm to about 50 nm, about 5 nm to about 100 nm, about 5 nm to about 150 nm, about 5 nm to about 200 nm, about 5 nm to about 250 nm, about 5 nm to about 300 nm, about 5 nm to about 350 nm, about 5 nm to about 400 nm, about 5 nm to about 450 nm, about 450 nm to about 500 nm, about 400 nm to about 500 nm, about 350 nm to about 500 nm, about 300 nm to about 500 nm, about 250 nm to about 500 nm, about 200 nm to about 500, about 150 nm to about 500 nm, about 100 nm to about 500 nm, or about 50 nm to about 500 nm. For example, about 5 nm to about 25 nm, about 25 nm to about 50 nm, about 40 nm to about 60 nm, about 50 to about 75 nm, or about 75 nm to about 100 nm.

In some embodiments, the particle is rod-shaped. As used herein, a "rod-shaped particle" can also refer to a rice-like particle, a worm-like particle, and a cylindrical particle. In some embodiments, the length of the particle is about 1 nm to about 2500 nm. For example, about 1 nm to about 200 nm, about 1 nm to about 400 nm, about 1 nm to about 600 nm, about 1 nm to about 800 nm, about 1 nm to about 1000 nm, about 1 nm to about 1200 nm, about 1 nm to about 1400 nm, about 1 nm to about 1600 nm, about 1 nm to about 1800 nm, about 1 nm to about 2000 nm, about 1 nm to about 2200 nm, about 1 nm to about 2400 nm, about 2300 nm to about 2500 nm, about 2100 nm to about 2500 nm, about 1900 nm to about 2500 nm, about 1700 nm to about 2500 nm, about 1500 nm to about 2500 nm, about 1300 nm to about 2500 nm, about 1100 nm to about 2500 nm, about 900 nm to about 2500 nm, about 700 nm to about 2500 nm, about 500 nm to about 2500 nm, about 300 nm to about 2500 nm, or about 100 nm to about 2500 nm. In some embodiments, the length of the particle is about 5 nm to about 500 nm. For example, about 5 nm to about 50 nm, about 5 nm to about 100 nm, about 5 nm to about 150 nm, about 5 nm to about 200 nm, about 5 nm to about 250 nm, about 5 nm to about 300 nm, about 5 nm to about 350 nm, about 5 nm to about 400 nm, about 5 nm to about 450 nm, about 450 nm to about 500 nm, about 400 nm to about 500 nm, about 350 nm to about 500 nm, about 300 nm to about 500 nm, about 250 nm to about 500 nm, about 200 nm to about 500, about 150 nm to about 500 nm, about 100 nm to about 500 nm, or about 50 nm to about 500 nm. For example, about 5 nm to about 25 nm, about 25 nm to about 50 nm, about 40 nm to about 60 nm, about 50 to about 75 nm, or about 75 nm to about 100 nm. In some embodiments, the rod-shaped particle has an aspect ratio (i.e., the ratio of length to width) of about 1 to about 8. For example an aspect ratio of about 1 to about 2, about 1 to about 3, about 1 to about 4, about 1 to about 5, about 1 to about 6, about 1 to about 7, about 7 to about 8, about 6 to about 8, about 5 to about 8, about 4 to about 8, about 3 to about 8, or about 2 to about 8. In some embodiments, the rod-shaped particle has an aspect ratio of about 1, about 1.5, about 2, about 2.5, about 3, about 3.5, about 4, about 4.5, about 5, about 5.5, about 6, about 6.5, about 7, or about 7.5.

In some embodiments, the particle is hydrophilic. In some embodiments, the particle is hydrophobic. In some embodiment, the particle is cationic. In some embodiments, the particle has a surface charge of about 1 to about 40 mV. In some embodiments, the particle is anionic. In some embodiments, the particle has a surface charge of about −1 to about −70 mV.

In some embodiments, the particle is thermo-responsive. For example, the hydrophobicity of a thermo-responsive particle can be controlled by temperature. The particles can also include surface modifications. Non-limiting examples of such surface modifications include cysteine-cyan5, a cationic monolayer, a nucleic acid, poly(isobutylene-alt-maleic anhydride), a coating with fetal bovine serum (FBS), citrate, 5-aminovaleric acid, L-DOPA, melatonin, serotonin-HCl, MUS/OT, glutathione/glucose, polyethyleneimine, or a combination thereof. See, e.g., Donahue. *Adv Drug Deliv Rev.* 143:68-96, 2019, which is incorporated herein by reference in its entirety.

In some instances, the small molecule can include a moiety sequence (e.g., a second barcode) (e.g., an oligonucleotide). In some instances, the moiety sequence (e.g., a second barcode) comprises a sequence that is unique to the small molecule (e.g., a unique molecular identifier (UMI) for the small molecule). In some instances, this UMI can be used to identify the presence of the small molecule in a biological sample (i.e., a cell). In some instances, the moiety sequence (e.g., a second barcode) further comprises a sequence that can hybridize to at least a portion or an entirety of a capture domain of a capture probe. In some embodiments, the small molecule includes a moiety sequence (e.g., a second barcode) that is conjugated or otherwise attached to the small molecule. In some embodiments, the moiety sequence (e.g., a second barcode) is covalently-linked to the small molecule. In some embodiments, a moiety sequence (e.g., a second barcode) is a nucleic acid sequence.

As used herein, the term "moiety sequence" (or "second barcode") refers to a barcode that is associated with or otherwise identifies the small molecule. In some embodiments, by identifying a small molecule and its associated moiety sequence, the analyte to which the small molecule binds can also be identified. A moiety sequence can be a nucleic acid sequence of a given length and/or sequence that is associated with the small molecule. A moiety sequence can generally include any of the variety of aspects of barcodes described herein.

In some embodiments, the moiety sequence comprises a region or moiety configured to hybridize to, bind to, couple to, or otherwise interact with a capture domain of a capture probe. In some embodiments, a moiety sequence includes a nucleic acid sequence that is complementary to or substantially complementary to the capture domain of a capture probe such that the moiety sequence hybridizes to the capture domain of the capture probe. In some embodiments, a moiety sequence comprises a poly(A) nucleic acid sequence that hybridizes to a capture domain that comprises a poly(T) nucleic acid sequence. In some embodiments, a moiety sequence comprises a poly(T) nucleic acid sequence that hybridizes to a capture domain that comprises a poly(A) nucleic acid sequence. In some embodiments, a moiety sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the moiety sequence.

In some embodiments of any of the spatial analysis methods described herein, the moiety sequence can be directly coupled to the small molecule, or it can be attached to a bead, molecular lattice, e.g., a linear, globular, cross-slinked, or other polymer, or other framework that is attached or otherwise associated with the small molecule, which allows attachment of multiple moiety sequences to a single small molecule. Attachment (coupling) of the moiety sequences to the small molecule can be achieved through any of a variety of direct or indirect, covalent or non-covalent associations or attachments. For example, in the case of a moiety sequence coupled to a small molecule that includes an antibody or antigen-binding fragment, such a moiety sequence can be covalently attached to a portion of the antibody or antigen-binding fragment using chemical conjugation techniques (e.g., Lightning-Link® antibody labelling kits available from Innova Biosciences). In some embodiments, a moiety sequence can be coupled to an antibody or antigen-binding fragment using non-covalent attachment mechanisms (e.g., using biotinylated antibodies and oligonucleotides or beads that include one or more biotinylated linker(s), coupled to oligonucleotides with an avidin or streptavidin linker.) Antibody and oligonucleotide biotinylation techniques can be used, and are described for example in Fang et al., Nucleic Acids Res. (2003), 31(2): 708-715, the entire contents of which is incorporated by reference herein. Likewise, protein and peptide biotinylation techniques have been developed and can be used, and are described for example in U.S. Pat. No. 6,265,552, the entire contents of which is incorporated by reference herein. Furthermore, click reaction chemistry such as a methyltetrazine-PEG5-NHS ester reaction, a TCO-PEG4-NHS ester reaction, or the like, can be used to couple moiety sequences to small molecules. The reactive moiety on the small molecule can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). Exemplary strategies to conjugate the small molecule to the moiety sequence include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation.

In some embodiments of any of the spatial profiling methods described herein, the moiety sequence coupled to a small molecule can include modifications that render it non-extendable by a polymerase. In some embodiments, when binding to a capture domain of a capture probe or nucleic acid in a sample for a primer extension reaction, the moiety sequence can serve as a template, not a primer. In some embodiments, the moiety sequence can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the moiety sequence includes a cleavable domain. For example, after the small molecule binds to an analyte (e.g., a cell surface analyte), the moiety sequence can be cleaved and collected for downstream analysis according to the methods as described herein. In some embodiments, the cleavable domain of the moiety sequence includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the small molecule(s) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell.

2. Generating Pooled Nucleic Acid Libraries

Also provided herein are methods of generating a library of genetically-perturbed cells. A genetically-perturbed cell can refer to any cell that has one or more genetic mutations including, but not limited to, a nucleotide deletion, insertion, or substitution. A cell comprising a moiety can be a genetically-perturbed cell. In some embodiments, a genetically-perturbed cell (i.e., a cell comprising a moiety) can refer to a cell that has a gene knockout and/or a gene knockdown. Methods of introducing a genetic perturbation into a cell and methods for generating a library of genetically-perturbed cells are known to one of skill in art. Such methods have been described in, for example, Liberali et al. Nat Rev Genet. 2015; and 16(1):18-32; and Boutros and Ahringer. Nat Rev Genet. 2008; 9(7):554-66.

In some embodiments, a cell comprising a moiety has been transduced with a vector, e.g., any of the vectors described herein. In some embodiments, a "genetically-perturbed cell" refers to a cell that has been transduced with a vector. In some embodiments, methods of introducing a genetic perturbation or moiety into a cell and/or methods for generating a library of genetically-perturbed cells include using a vector. In some embodiments, the vector is not integrated into the host cell's genome. In some embodiments, the vector is integrated into the host cell's genome.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. In some embodiments, a cell comprising a moiety has been transduced with a vector from a vector library. In some embodiments, a "genetically-perturbed cell" refers to a cell that has been transduced with a vector from a vector library.

In some embodiments, the vector comprises a moiety sequence (e.g., a second barcode). The moiety sequence was described in part (1) of this section and the embodiments disclosed therein are incorporated herein. For instance, in some embodiments, the moiety sequence is substantially complementary to the capture domain. In some embodiments, the moiety sequence is a polyadenylated sequence. In some instances, the moiety sequence of the vector comprises a sequence that uniquely identifies the vector (i.e., a UMI specific to the vector).

In some embodiments, the vector or library of vectors is a lentiviral vector. In some embodiments, a clustered regularly interspaced short palindromic repeats (CRISPR)-based perturbation is introduced into a cell. For example, a CRISPR lentiviral vector can be used to introduce a genetic perturbation into a cell. In some embodiments, a CRISPR lentiviral vector can include a guide RNA (gRNA). In some embodiments, a CRISPR lentiviral vector can include a single guide RNA (sgRNA).

Figure 13:
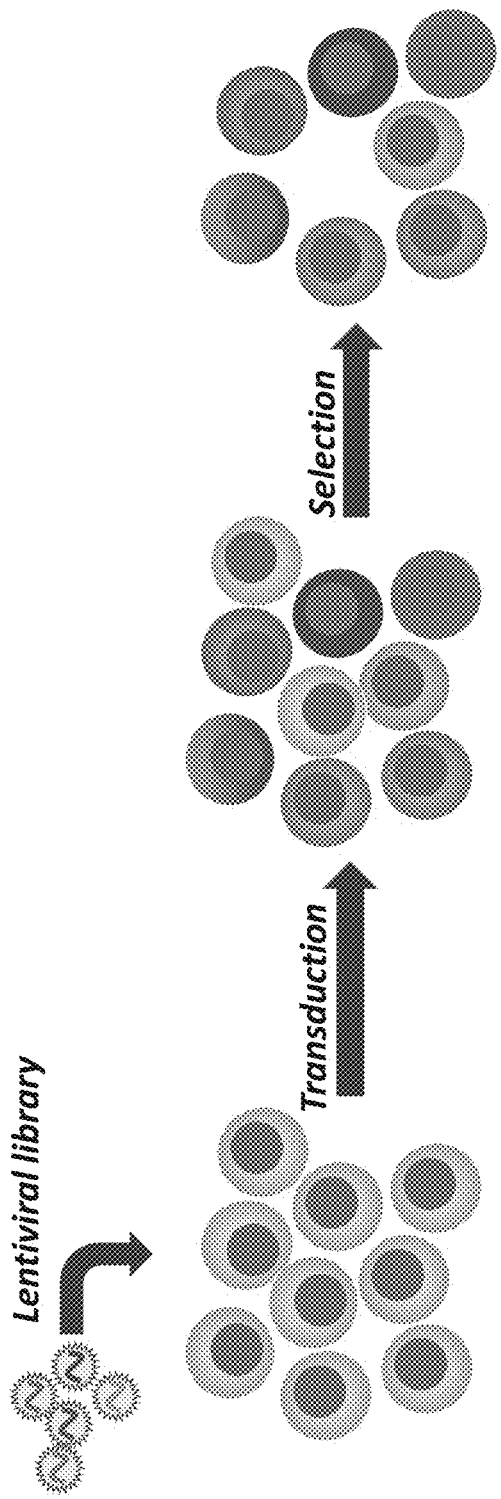
FIG. 13 is a schematic depicting multiplexed alteration of mammalian cells.

In some embodiments, pluralities of genetically-perturbed cells can be produced using a library of lentiviral vectors. In some embodiments, cells can be transduced with a library of lentiviral vectors to form genetically-perturbed cells, and the genetically-perturbed cells can be selected from the cells that did not receive a lentiviral vector (see, for example, FIG. 13). In some embodiments, the library of lentiviral vectors is a library of CRISPR lentiviral vectors. Methods of delivering genetic material, include CRISPR lentiviral vectors, are discussed in Lino et al., *Drug Deliv.* 2018; 25(1):1234-1257; and McDade et al. *Curr Protoc Mol Biol.* 2016; 115:31.5.1-31.5.13, each of which is herein incorporated by reference in its entirety. In some embodiments, a library of CRISPR lentiviral vectors includes at least two pluralities of CRISPR lentiviral vectors, wherein a plurality of CRISPR lentiviral vectors includes a different gRNA and/or sgRNA from another plurality of CRISPR lentiviral vectors. In some embodiments, wherein a library of CRISPR lentiviral vectors includes at least two pluralities of CRISPR lentiviral vectors, each plurality of CRISPR lentiviral vectors includes a different gRNA and/or sgRNA from each other plurality of CRISPR lentiviral vectors.

In some embodiments a clustered regularly interspaced short palindromic repeats (CRISPR)-based perturbation is introduced into a cell. For example, a CRISPR lentiviral vector can be used to introduce a genetic perturbation into a cell. In some embodiments, a CRISPR lentiviral vector can include a guide RNA (gRNA). In some embodiments, a CRISPR lentiviral vector can include a single guide RNA (sgRNA).

In some embodiments, the vector in the lentiviral library includes a barcode sequence. In some embodiments, the vector includes a barcode sequence. In some embodiments, a vector includes more than one unique barcode (e.g., at least 2, 3, 4, 5, 6, 7, 8, 9, 10, about 15, about 20, about 30, about 40, or about 50 unique barcodes). In some embodiments, a vector includes multiple copies of a unique barcode (e.g., about 10 copies, about 50, about 100, about 500, about 1000 or more). In some embodiments, identification of the barcode provides information regarding the spatial location of a particular biological analyte. In some embodiments, the barcode includes a capture domain sequence as disclosed herein. In some embodiments, the capture domain sequence is a poly(dT) sequence. In some embodiments, the capture domain sequence is a degenerate sequence. In some embodiments, the capture domain sequence is particular to a target sequence of interest. In some embodiments, the barcode includes a cleavage domain as disclosed herein. In some embodiments, the barcode includes a functional domain as disclosed herein. In some embodiments, the functional domain is a primer sequence. In some embodiments, the barcode includes a spatial barcode as disclosed herein. In some embodiments, the barcode includes a unique molecular identifier (UMI) as disclosed herein.

In some embodiments, a vector as disclosed herein expresses a gene of interest. In some embodiments, the gene of interest encodes for a protein that functions in a cellular pathway. For example, in some embodiments, the vector encodes for an inhibitor, antagonist, or agonist of various cellular pathways, including for example, pathways involving DNA damage/DNA repair, cell cycle/checkpoints, JAK/STAT signaling, MAPK signaling, GPCR/G protein, angiogenesis, immunology and inflammation, endocrinology and hormones, cancer, metabolism, and stem cells.

(c) Biological Samples

Methods disclosed herein can be performed on any type of sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample.

Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy. In some instances, the biological sample can include one or more diseased cells. A diseased cell can have altered metabolic properties, gene expression, protein expression, and/or morphologic features. Examples of diseases include inflammatory disorders, metabolic disorders, nervous system disorders, and cancer. In some instances, the biological sample includes cancer or tumor cells. Cancer cells can be derived from solid tumors, hematological malignancies, cell lines, or obtained as circulating tumor cells. In some instances, the biological sample is a heterogenous sample. In some instances, the biological sample is a heterogenous sample that includes tumor or cancer cells and/or stromal cells, In some instances, the cancer is breast cancer. In some instances, the breast cancer is triple positive breast cancer (TPBC). In some instances, the breast cancer is triple negative breast cancer (TNBC).

In some instances, the cancer is colorectal cancer. In some instances, the cancer is ovarian cancer. In certain embodiments, the cancer is squamous cell cancer, small-cell lung cancer, non-small cell lung cancer, gastrointestinal cancer, Hodgkin's or non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, or a type of head or neck cancer. In certain embodiments, the cancer treated is desmoplastic melanoma, inflammatory breast cancer, thymoma, rectal cancer, anal cancer, or surgically treatable or non-surgically treatable brain stem glioma. In some embodiments, the subject is a human.

FFPE samples generally are heavily cross-linked and fragmented, and therefore this type of sample allows for limited RNA recovery using conventional detection techniques. In certain embodiments, methods of targeted RNA capture provided herein are less affected by RNA degradation associated with FFPE fixation than other methods (e.g., methods that take advantage of oligo-dT capture and reverse transcription of mRNA). In certain embodiments, methods provided herein enable sensitive measurement of specific genes of interest that otherwise might be missed with a whole transcriptomic approach.

In some instances, FFPE samples are stained (e.g., using H&E). The methods disclosed herein are compatible with H&E will allow for morphological context overlaid with transcriptomic analysis. However, depending on the need some samples may be stained with only a nuclear stain, such as staining a sample with only hematoxylin and not eosin, when location of a cell nucleus is needed.

In some embodiments, a biological sample (e.g. tissue section) can be fixed with methanol, stained with hematoxylin and eosin, and imaged. In some embodiments, fixing, staining, and imaging occurs before one or more probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

In some embodiments, the FFPE sample is deparaffinized, permeabilized, equilibrated, and blocked before target probe oligonucleotides are added. In some embodiments, deparaffinization using xylenes. In some embodiments, deparaffinization includes multiple washes with xylenes. In some embodiments, deparaffinization includes multiple washes with xylenes followed by removal of xylenes using multiple rounds of graded alcohol followed by washing the sample with water. In some aspects, the water is deionized water. In some embodiments, equilibrating and blocking includes incubating the sample in a pre-Hyb buffer. In some embodiments, the pre-Hyb buffer includes yeast tRNA. In some embodiments, permeabilizing a sample includes washing the sample with a phosphate buffer. In some embodiments, the buffer is PBS. In some embodiments, the buffer is PBST.

For the purpose of this disclosure, an "analyte" can include any biological substance, structure, moiety, or component to be analyzed. The term "target" can similarly refer to an analyte of interest. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, analyte(s) can be peptides or proteins, including without limitation antibodies and enzymes. In some embodiments, the analyte is a protein.

(d) Imaging and Preparation of Biological a Sample
(i) Imaging and Staining

Prior to addition of the probes, in some instances, biological samples can be stained using a wide variety of stains and staining techniques. In some instances, the biological sample is a section on a slide (e.g., a 10 µm section). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) on the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 minutes at 4° C.) before being stained with fluorescent primary antibodies (1:100 in 3×SSC, 2% BSA, 0.1% Triton X, 1 U/µl RNAse inhibitor for 30 minutes at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

In some embodiments, the methods described herein further include imaging the cell comprising the moiety (e.g., any of the moieties described herein). Imaging can be used, for example, to determine the morphology of the cell comprising the moiety at a distinct spatial position on the substrate. In some embodiments, the morphology is correlated to a biological analyte of the cell comprising the moiety using the methods described herein. In some embodiments, the morphology is correlated to a perturbation in the cell comprising the moiety. For example, the morphology is correlated to a change in one or more biological analytes compared to a cell including a different moiety or a cell not including the moiety.

(ii) Preparation of Samples for Application of Pooled Libraries

In some instances, the biological sample is deparaffinized. Deparaffinization can be achieved using any method known in the art. For example, in some instances, the biological sample is treated with a series of washes that include xylene and various concentrations of ethanol. In some instances, methods of deparaffinization include treatment with xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1× PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA such as from brewer's yeast (e.g., at a final concentration of 10-20 µg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

(e) Manipulation of Biological Samples using Pooled Libraries (i) Manipulation of Biological Samples using a Pooled Small Molecule Library Methods of identifying the small molecule introduced into the cell are also known to one of skill in the art. For example, in some embodiments, a moiety sequence (e.g., a second barcode) can be introduced into the cell using a particle (e.g., the particle includes the small molecule). In some embodiments, the particle further includes a moiety sequence. In some embodiments, the particle includes more than one unique moiety sequence (e.g., at least 2, 3, 4, 5, 6, 7, 8, 9, 10, about 15, about 20, about 30, about 40, about 50, about 75, or about 100 unique moiety sequences). In some embodiments, the particle includes multiple copies of a unique moiety sequence (e.g., about 10, about 50, about 100, about 500, about 1000 or more). In some embodiments, the moiety sequence is a nucleotide sequence that identifies the small molecule. In some embodiments, identification of the moiety sequence provides information regarding the spatial location of a particular biological analyte. In some embodiments, the moiety sequence includes a capture domain sequence as disclosed herein. In some embodiments, the capture domain sequence is a poly(dT) sequence. In some embodiments, the capture domain sequence is a degenerate sequence. In some embodiments, the capture domain sequence is particular to a target sequence of interest. In some embodiment, the moiety sequence includes a cleavage domain as disclosed herein. In some embodiments, the moiety sequence includes a functional domain as disclosed herein. In some embodiments, the functional domain is a primer sequence. In some embodiment, the moiety sequence includes a spatial barcode as disclosed herein. In some embodiment, the moiety sequence includes a unique molecular identifier (UMI) as disclosed herein.

Determining the identity of the moiety sequence (e.g., second barcode) that was introduced into the cell can be used to identify the small molecule introduced into the cell. In some embodiments, the moiety sequence can be part of a polyadenylated sequence. Introducing a polyadenylated moiety sequence into the cell can allow the moiety sequence to be sequenced and identified using the methods described herein. See also, for example, Adamson et al. *Cell.* 167(7): 1867-1882.e21, 2016; Datlinger et al. *Nat Methods.* 14(3): 297-301, 2017; Jaitin et al. *Cell.* 167(7):1883-1896.e15, 2016; and Dixit et al. *Cell.* 167(7):1853-1866.e17, 2016, all of which are incorporated by reference herein in their entireties. As such, correlating a biological analyte from a cell including a small molecule with a first barcode of a capture probe at a distinct spatial position of a substrate can further include correlating the small molecule of the cell to a distinct spatial position of the substrate using the moiety sequence that identifies the small molecule of the cell.

In some embodiments, the methods described herein can include profiling biological analytes from a cell (or a group of cells) that includes one or more small molecules (or a library of small molecules that are all identical or that are different).

In some embodiments, the methods described herein can include one or more pluralities of cells including one or more small molecules (e.g., a library of cells including small molecules). For example, the methods described herein can be useful in detecting one or more biological analytes in cells perturbed by a library of small molecules, e.g., methods using one or more pools of small molecules. Pooling schemes are known to those in the art, see, e.g., Kainkaryam. Curr Opin Drug Discov Devel. 2009 May; 12(3): 339-350, which is incorporated herein by reference in its entirety. Accordingly, in some embodiments, a method to spatially profile one or more biological analytes present in a library of cells including a small molecule can include contacting the library of cells including a small molecule with a substrate including a plurality of capture probes, wherein a capture probe of the plurality includes a first barcode and a capture domain; releasing the one or more biological analytes from members of the library of cells including a small molecule, wherein the one or more biological analytes are bound by capture probes at distinct spatial positions of the substrate; detecting the one or more biological analytes bound by capture probes; and correlating each biological analyte with the first barcode from the capture probe it was bound to at the distinct spatial position of the substrate; thus profiling the one or more biological analytes as present in the library of cells including a small molecule at one or more distinct spatial positions. In some embodiments, one biological analyte is bound to one capture probe.

In some embodiments, the methods described herein can include profiling biological analytes from a cell that includes multiple, identical small molecules. In some embodiments, the methods described herein can include profiling biological analytes from a cell that includes multiple, unique (i.e., different) small molecules. In some embodiments, the methods described herein can include profiling biological analytes from a group of cells that each include a single small molecule. In some embodiments, the methods described herein can include profiling biological analytes from a group of cells, each of which includes multiple copies of the same small molecule. In some embodiments, the methods described herein can include profiling biological analytes from a group of cells that each include multiple copies of different small molecules.

In some embodiments, the methods disclosed herein also include a wash step. The wash step removes any unbound probes. Wash steps could be performed between any of the steps in the methods disclosed herein. For example, a wash step can be performed after adding probes to the biological sample. As such, free/unbound probes are washed away, leaving only probes that have hybridized to an analyte. In some instances, multiple (i.e., at least 2, 3, 4, 5, or more) wash steps occur between the methods disclosed herein. Wash steps can be performed at times (e.g., 1, 2, 3, 4, or 5 minutes) and temperatures (e.g., room temperature) known in the art and determined by a person of skill in the art.

In some instances, wash steps are performed using a wash buffer. In some instances, the wash buffer includes SSC (e.g., 1×SSC). In some instances, the wash buffer includes PBS (e.g., 1×PBS). In some instances, the wash buffer includes PBST (e.g., 1×PBST). In some instances, the wash buffer can also include formamide or be formamide free.

In some embodiments, a biological sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves separating the fragments into individual partitions (e.g., fluid droplets), and then analyzing the contents of the partitions. In general, each partition maintains separation of its own contents from the contents of other partitions. The partition can be a droplet in an emulsion, for example.

Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids. In some embodiments, a microfluidical channel structure can be used for partitioning individual analytes (e.g., cells)

into discrete partitions. For example, a first aqueous fluid that includes suspended biological particles (or cells) may be transported along a channel segment into a junction, while a second fluid that is immiscible with the first aqueous fluid is delivered to the junction from each of the channel segments to create discrete droplets of the first aqueous fluid flowing into a channel segment, and flowing away from the junction. The channel segment may be fluidically coupled to an outlet reservoir where the discrete droplets can be stored and/or harvested. A discrete droplet generated may include an individual biological particle. A discrete droplet generated may include more than one individual biological particle. A discrete droplet may contain no biological particle. Each discrete partition may maintain separation of its own contents (e.g., individual biological particle) from the contents of other partitions.

In some embodiments, one or more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well.

Figure 8:
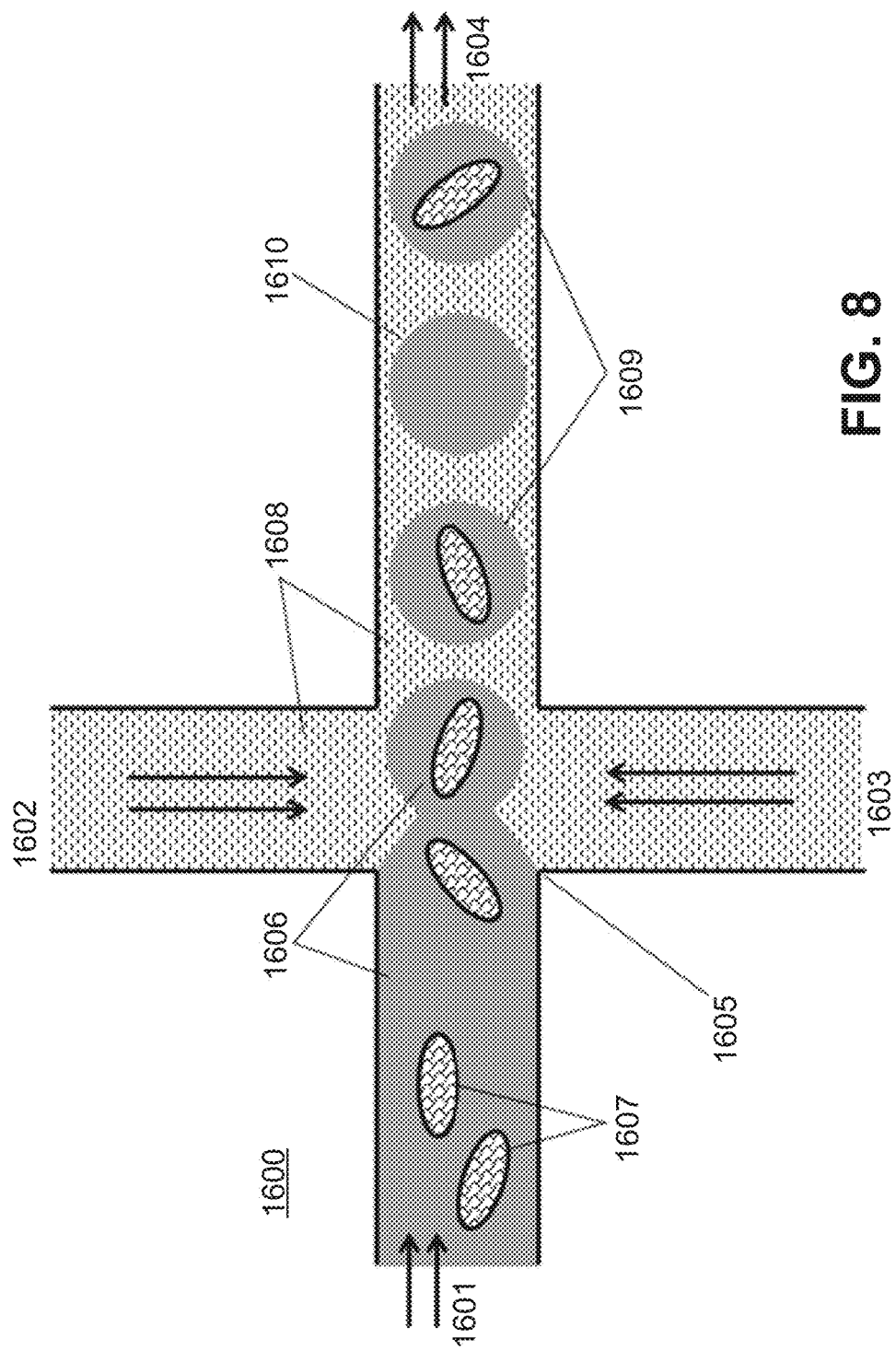
FIG. 8 shows an example of a microfluidic channel structure 800 for partitioning dissociated sample (e.g., biological particles or individual cells from a sample).

FIG. 8 shows an example of a microfluidic channel structure for partitioning individual analytes (e.g., cells) into discrete partitions. The channel structure can include channel segments 801, 802, 803, and 804 communicating at a channel junction 805. In operation, a first aqueous fluid 806 that includes suspended biological particles (or cells) 807 may be transported along channel segment 801 into junction 805, while a second fluid 808 that is immiscible with the aqueous fluid 806 is delivered to the junction 805 from each of channel segments 802 and 803 to create discrete droplets 809, 810 of the first aqueous fluid 806 flowing into channel segment 804, and flowing away from junction 805. The channel segment 804 may be fluidically coupled to an outlet reservoir where the discrete droplets can be stored and/or harvested. A discrete droplet generated may include an individual biological particle 807 (such as droplets 809). A discrete droplet generated may include more than one individual biological particle 807. A discrete droplet may contain no biological particle 807 (such as droplet 810). Each discrete partition may maintain separation of its own contents (e.g., individual biological particle 807) from the contents of other partitions.

Figure 9A:
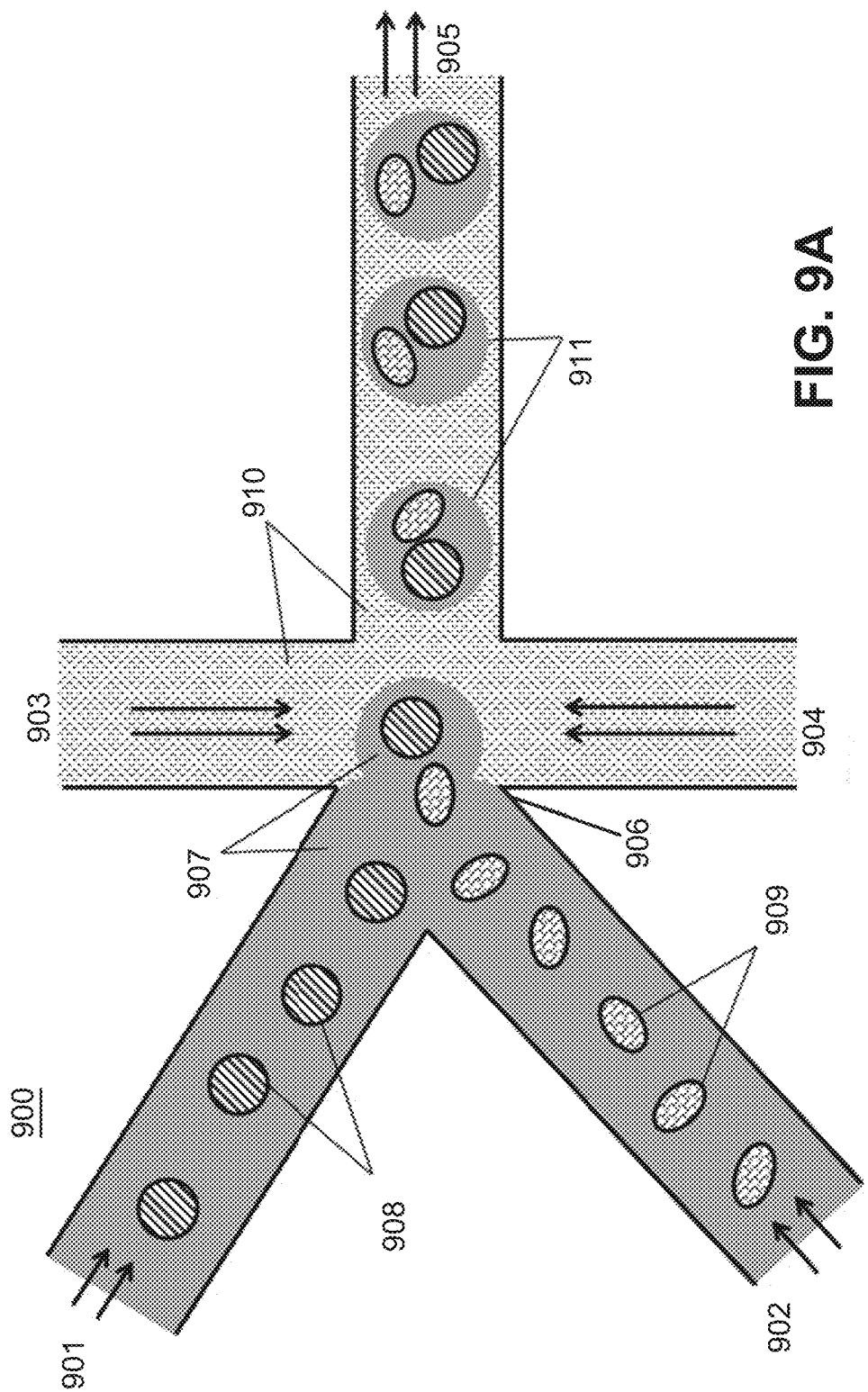
FIGS. 9A-C shows 9A) an example of a microfluidic channel structure 900 for delivering spatial barcode carrying beads to droplets, 9B) shows a cross-section view of another example of a microfluidic channel structure 950 with a geometric feature for controlled partitioning, and 9C) shows an example of a workflow schematic.

FIG. 9A shows another example of a microfluidic channel structure 900 for delivering beads to droplets. The channel structure includes channel segments 901, 902, 903, 904, and 905 communicating at a channel junction 906. During operation, the channel segment 901 can transport an aqueous fluid 907 that includes a plurality of beads 908 along the channel segment 901 into junction 906. The plurality of beads 908 can be sourced from a suspension of beads. For example, the channel segment 901 can be connected to a reservoir that includes an aqueous suspension of beads 908. The channel segment 902 can transport the aqueous fluid 907 that includes a plurality of particles 909 (e.g., cells) along the channel segment 902 into junction 906. In some embodiments, the aqueous fluid 907 in either the first channel segment 901 or the second channel segment 902, or in both segments, can include one or more reagents, as further described below.

A second fluid 910 that is immiscible with the aqueous fluid 907 (e.g., oil) can be delivered to the junction 906 from each of channel segments 903 and 904. Upon meeting of the aqueous fluid 907 from each of channel segments 901 and 902 and the second fluid 910 from each of channel segments 903 and 904 at the channel junction 906, the aqueous fluid 907 can be partitioned as discrete droplets 911 in the second fluid 910 and flow away from the junction 906 along channel segment 905. The channel segment 905 can deliver the discrete droplets to an outlet reservoir fluidly coupled to the channel segment 905, where they can be harvested.

As an alternative, the channel segments 901 and 902 can meet at another junction upstream of the junction 906. At such junction, beads and biological particles can form a mixture that is directed along another channel to the junction 906 to yield droplets 911. The mixture can provide the beads and biological particles in an alternating fashion, such that, for example, a droplet includes a single bead and a single biological particle.

The second fluid 910 can include an oil, such as a fluorinated oil, that includes a fluorosurfactant for stabilizing the resulting droplets, for example, inhibiting subsequent coalescence of the resulting droplets 911.

The partitions described herein can include small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. In the foregoing discussion, droplets with beads were formed at the junction of different fluid streams. In some embodiments, droplets can be formed by gravity-based partitioning methods.

Figure 9B:
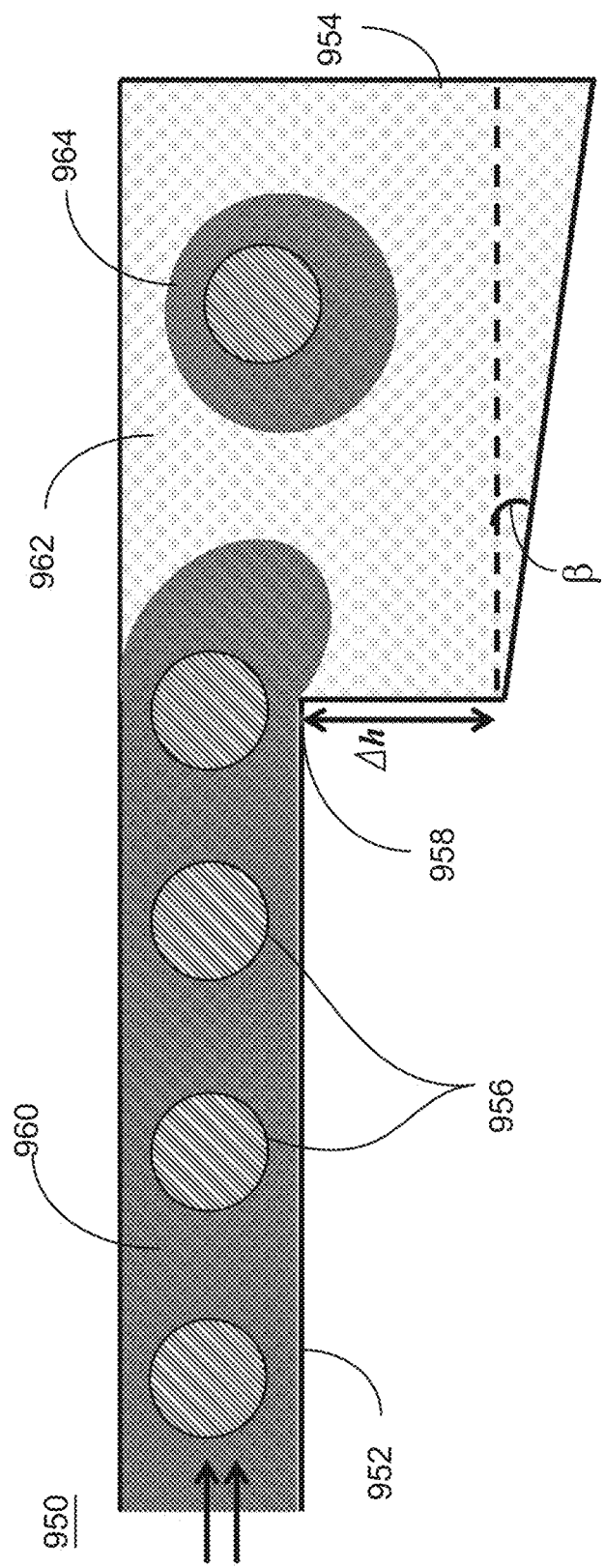

FIG. 9B shows a cross-section view of another example of a microfluidic channel structure 950 with a geometric feature for controlled partitioning. A channel structure 950 can include a channel segment 952 communicating at a channel junction 958 (or intersection) with a reservoir 954. In some instances, the channel structure 950 and one or more of its components can correspond to the channel structure 900 and one or more of its components.

An aqueous fluid 960 comprising a plurality of particles 956 may be transported along the channel segment 952 into the junction 958 to meet a second fluid 962 (e.g., oil, etc.) that is immiscible with the aqueous fluid 960 in the reservoir 954 to create droplets 964 of the aqueous fluid 960 flowing into the reservoir 954. At the junction 958 where the aqueous fluid 960 and the second fluid 962 meet, droplets can form based on factors such as the hydrodynamic forces at the junction 958, relative flow rates of the two fluids 960, 962, fluid properties, and certain geometric parameters (e.g., $\Delta h$, etc.) of the channel structure 950. A plurality of droplets can be collected in the reservoir 954 by continuously injecting the aqueous fluid 960 from the channel segment 952 at the junction 958.

A discrete droplet generated may comprise one or more particles of the plurality of particles 956. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 960 can have a substantially uniform concentration or frequency of particles 956. As described elsewhere herein, the particles 956 (e.g., beads) can be introduced into the channel segment 952 from a separate channel (not shown in FIGS. 9A-9B). The frequency of particles 956 in the channel segment 952 may be controlled by controlling the frequency in which the particles 956 are introduced into the channel segment 952 and/or the relative flow rates of the fluids in the channel segment 952 and the separate channel. In some instances, the particles 956 can be introduced into the channel segment 952 from a plurality of different channels, and the frequency controlled accordingly. In some instances, different particles may be introduced via separate channels. For example, a first separate channel can introduce beads and a second separate channel can introduce biological particles into the channel segment 952. The first separate channel introducing the beads may be upstream or downstream of the second separate channel introducing the biological particles.

In some instances, the second fluid 962 may not be subjected to and/or directed to any flow in or out of the reservoir 954. For example, the second fluid 962 may be substantially stationary in the reservoir 954. In some instances, the second fluid 962 may be subjected to flow within the reservoir 954, but not in or out of the reservoir 954, such as via application of pressure to the reservoir 954 and/or as affected by the incoming flow of the aqueous fluid 960 at the junction 958. Alternatively, the second fluid 962 may be subjected and/or directed to flow in or out of the reservoir 954. For example, the reservoir 954 can be a channel directing the second fluid 962 from upstream to downstream, transporting the generated droplets.

The channel structure 950 at or near the junction 958 may have certain geometric features that at least partly determine the volumes and/or shapes of the droplets formed by the channel structure 950. The channel segment 952 can have a first cross-section height, h1, and the reservoir 954 can have a second cross-section height, h2. The first cross-section height, h1, and the second cross-section height, h2, may be different, such that at the junction 958, there is a height difference of $\Delta h$. The second cross-section height, h2, may be greater than the first cross-section height, h1. In some instances, the reservoir may thereafter gradually increase in cross-section height, for example, the more distant it is from the junction 958. In some instances, the cross-section height of the reservoir may increase in accordance with expansion angle, $\beta$, at or near the junction 958. The height difference, $\Delta h$, and/or expansion angle, $\beta$, can allow the tongue (portion of the aqueous fluid 960 leaving channel segment 952 at junction 958 and entering the reservoir 954 before droplet formation) to increase in depth and facilitate decrease in curvature of the intermediately formed droplet. For example, droplet volume may decrease with increasing height difference and/or increasing expansion angle.

The height difference, $\Delta h$, can be at least about 1 µm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 µm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 µm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 960 entering the junction 958 can be between about 0.04 microliters (µL)/minute (min) and about 40 µL/min. In some instances, the flow rate of the aqueous fluid 960 entering the junction 958 can be between about 0.01 microliters (µL)/ minute (min) and about 100 µL/min. Alternatively, the flow rate of the aqueous fluid 960 entering the junction 958 can be less than about 0.01 µL/min. alternatively, the flow rate of the aqueous fluid 960 entering the junction 958 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 microliters/minute, the droplet radius may not be dependent on the flow rate of the aqueous fluid 960 entering the junction 958. The second fluid 962 may be stationary, or substantially stationary, in the reservoir 954. Alternatively, the second fluid 962 may be flowing, such as at the above flow rates described for the aqueous fluid 960.

While FIG. 9B illustrates the height difference, $\Delta h$, being abrupt at the junction 958 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 958, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIG. 9B illustrates the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

Figure 9C:
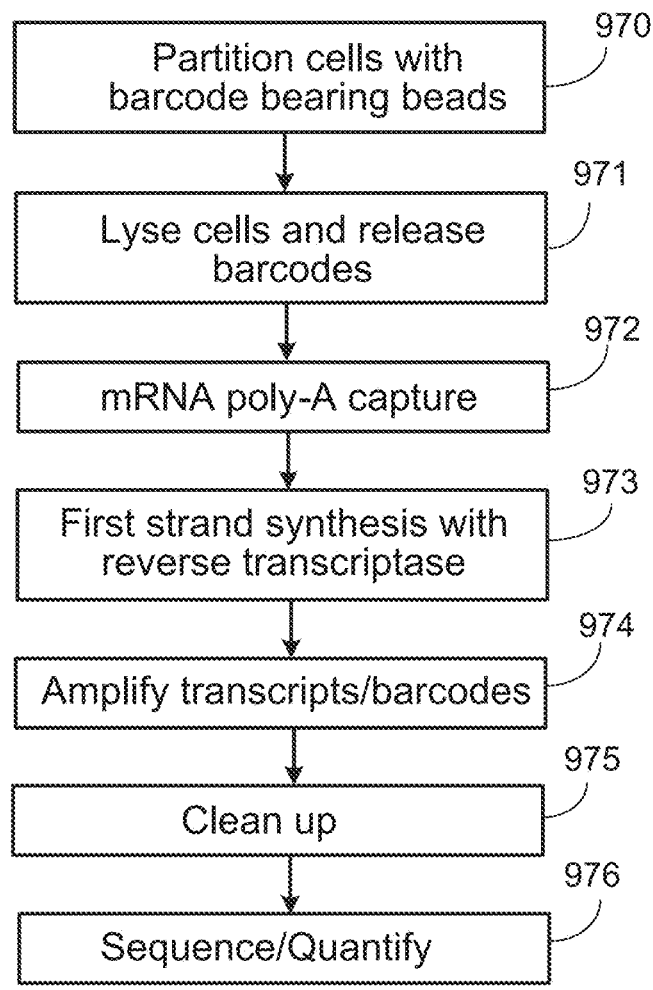

FIG. 9C depicts a workflow wherein cells are partitioned into droplets along with barcode-bearing beads 970. See FIG. 9A. The droplet forms an isolated reaction chamber wherein the cells can be lysed 971 and target analytes within the cells can then be captured 972 and amplified 973, 974 according to previously described methods. After sequence library preparation clean-up 975, the material is sequenced and/or quantified 976 according to methods described herein. For example, the workflow shown in FIG. 9C can be used with a biological sample on an array, where the features of the array have been delivered to the substrate via a droplet manipulation system. In some embodiments, capture probes on the features can specifically bind analytes present in the biological sample. In some embodiments, the features can be removed from the substrate (e.g., removed by any method described herein) and partitioned into droplets with barcode-bearing beads for further analysis according to methods described herein.

It should be noted that while the example workflow in FIG. 9C includes steps specifically for the analysis of mRNA, analogous workflows can be implemented for a wide variety of other analytes, including any of the analytes described previously.

By way of example, in the context of analyzing sample RNA as shown in FIG. 9C, the poly(T) segment of one of the released nucleic acid molecules (e.g., from the bead) can hybridize to the poly(A) tail of an mRNA molecule. Reverse transcription can result in a cDNA transcript of the mRNA, which transcript includes each of the sequence segments of the nucleic acid molecule. If the nucleic acid molecule includes an anchoring sequence, it will more likely hybridize to and prime reverse transcription at the sequence end of the poly(A) tail of the mRNA.

(ii) Manipulation of Biological Samples Using a Pooled Nucleic Acid Library

Methods of identifying a genetic perturbation or genetic moiety introduced into a cell are also known to one of skill in the art. See, for example, Adamson et al. *Cell.* 167(7): 1867-1882.e21, 2016; Datlinger et al. *Nat Methods.* 14(3): 297-301, 2017; Jaitin et al. *Cell.* 167(7):1883-1896.e15, 2016; and Dixit et al. *Cell.* 167(7):1853-1866.e17, 2016, each of which is incorporated by reference herein in its entirety.

In some instances, the methods include introducing the pooled nucleic acid library into a cell or plurality of cells. The term "introducing," as used herein, includes delivery of a vector or pooled library to a cell or cells. Such introducing may take place in vivo, in vitro, or ex vivo. A vector for expression of a gene product may be introduced into a cell by transfection, which typically means insertion of heterologous DNA into a cell by physical means (e.g., calcium phosphate transfection, electroporation, microinjection, or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

After introduction, the methods in some instances can include determining the presence of a genetic moiety (i.e., a nucleic acid (e.g., gRNA and/or sgRNA)) that was introduced into a cell. For example, a moiety sequence (e.g., a second barcode) can be introduced into the genetically-perturbed cell that identifies the genetic moiety in the cell (e.g., identifies the gRNA introduced into the cell) and/or a polyadenylated nucleotide sequence, such as a polyadenylated gRNA sequence, can be introduced into the genetically-perturbed cell. In some embodiments, the moiety sequence can be part of a polyadenylated sequence. Introducing a polyadenylated barcode sequence and/or a polyadenylated gRNA sequence into the cell can allow the second barcode and/or gRNA sequence to be sequenced and identified using the methods described herein. In some embodiments, the CRISPR lentiviral vector can further include the moiety sequence identifying the gRNA and/or a polyadenylated or an oligo (dT) nucleotide sequence (e.g., a polyadenylated gRNA sequence). As such, correlating a biological analyte from a genetically-perturbed cell with a first barcode of a capture probe at a distinct spatial position of a substrate can further include correlating the genetic perturbation of the cell to a distinct spatial position of the substrate using the moiety sequence that identifies the genetic perturbation of the cell and/or the polyadenylated nucleotide sequence. In addition, also disclosed herein are methods of selecting a cell that includes the genetic perturbation.

In some embodiments, the methods described herein can include profiling biological analytes from one or more pluralities of genetically-perturbed cells (e.g., a library of genetically-perturbed cells). For example, a method to spatially profile one or more biological analytes present in a library of genetically-perturbed cells can include contacting the library of genetically-perturbed cells with a substrate including a plurality of capture probes, wherein a capture probe of the plurality includes a first barcode and a capture domain; releasing the one or more biological analytes from members of the library of genetically-perturbed cells, wherein the one or more biological analytes are bound by capture probes at distinct spatial positions of the substrate; detecting the one or more biological analytes bound by capture probes; and correlating each biological analyte with the first barcode from the capture probe it was bound to at the distinct spatial position of the substrate; thus profiling the one or more biological analytes as present in the library of genetically-perturbed cells at distinct spatial positions. In some embodiments, one biological analyte is bound to one capture probe.

In some embodiments, a plurality of genetically-perturbed cells includes a different genetic perturbation from another plurality of genetically-perturbed cells. In some embodiments, each plurality of genetically-perturbed cells includes a different genetic perturbation from each other plurality of genetically-perturbed cells. In some embodiments, a plurality of genetically-perturbed cells with a different genetic perturbation from another plurality of genetically-perturbed cells also has a different polyadenylated barcode sequence and/or a polyadenylated gRNA sequence from the other plurality of genetically-perturbed cells (e.g., the polyadenylated barcode sequence and/or a polyadenylated gRNA sequence can identify the genetic perturbation of the cell). In some embodiments, each plurality of genetically-perturbed cells that has a different genetic perturbation from each other plurality of genetically-perturbed cells also has a different polyadenylated barcode sequence and/or a polyadenylated gRNA sequence from each other plurality of genetically-perturbed cells (e.g., the polyadenylated barcode sequence and/or a polyadenylated gRNA sequence can identify the genetic perturbation of the cell).

In some embodiments, the methods disclosed herein also include a wash step. The wash step removes any unbound probes. Wash steps could be performed between any of the steps in the methods disclosed herein. For example, a wash step can be performed after adding probes to the biological sample. As such, free/unbound probes are washed away, leaving only probes that have hybridized to an analyte. In some instances, multiple (i.e., at least 2, 3, 4, 5, or more) wash steps occur between the methods disclosed herein. Wash steps can be performed at times (e.g., 1, 2, 3, 4, or 5 minutes) and temperatures (e.g., room temperature) known in the art and determined by a person of skill in the art.

In some instances, wash steps are performed using a wash buffer. In some instances, the wash buffer includes SSC (e.g., 1×SSC). In some instances, the wash buffer includes PBS (e.g., 1×PBS). In some instances, the wash buffer includes PBST (e.g., 1×PBST). In some instances, the wash buffer can also include formamide or be formamide free.

In some embodiments, a biological sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves separating the fragments into individual partitions (e.g., fluid droplets), and then analyzing the contents of the partitions. In general, each partition maintains separation of its own contents from the contents of other partitions. The partition can be a droplet in an emulsion, for example.

Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids. In some embodiments, a microfluidical channel structure can be used for partitioning individual analytes (e.g., cells) into discrete partitions. For example, a first aqueous fluid that includes suspended biological particles (or cells) may be transported along a channel segment into a junction, while a second fluid that is immiscible with the first aqueous fluid is delivered to the junction from each of the channel segments to create discrete droplets of the first aqueous fluid flowing into a channel segment, and flowing away from the junction. The channel segment may be fluidically coupled to an outlet reservoir where the discrete droplets can be stored and/or harvested. A discrete droplet generated may include an individual biological particle. A discrete droplet generated may include more than one individual biological particle. A discrete droplet may contain no biological particle. Each discrete partition may maintain separation of its own contents (e.g., individual biological particle) from the contents of other partitions. Microfluidic systems have been described in part (1) of this section and is incorporated herein.

(e) Spatial Detection of Manipulated Cells

After an analyte and/or moiety from the cell, e.g., a cell in a biological sample, has hybridized or otherwise been associated with a capture probe according to any of the methods described above in connection with the general spatial cell-based analytical methodology, the barcoded constructs that result from hybridization/association are analyzed.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to a capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by uracil-DNA glycosylase, apurinic/apyrimidinic (AP) endonuclease (APE1), uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Lucigen, Middleton, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not specially bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and specifically bind (e.g., hybridize) to an extended capture probe. In some embodiments, about 1 to about 10 probes can be contacted to the substrate and specifically bind (e.g., hybridize) to an extended capture probe. In some embodiments, about 10 to about 100 probes can be contacted to the substrate and specifically bind (e.g., hybridize) to an extended capture probe. In some embodiments, about 20 to about 90 probes can be contacted to the substrate and specifically bind (e.g., hybridize) to an extended capture probe. In some embodiments, about 30 to about 80 probes (e.g., detectable probes) can be contacted to the substrate and specifically bind (e.g., hybridize) to an extended capture probe. In some embodiments, about 40 to about 70 probes can be contacted to the substrate and specifically bind (e.g., hybridize) to an extended capture probe. In some embodiments, about 50 to about 60 probes can be contacted to the substrate and specifically bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and specifically bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

In some instances, the ligated probe and capture probe can be amplified or copied, creating a plurality of cDNA molecules. In some embodiments, cDNA can be denatured from the capture probe template and transferred (e.g., to a clean tube) for amplification, and/or library construction. The spatially-barcoded cDNA can be amplified via PCR prior to library construction. The cDNA can then be enzymatically fragmented and size-selected in order to optimize for cDNA amplicon size. P5 and P7 sequences directed to capturing the amplicons on a sequencing flowcell (e.g., Illumina sequencing instruments) can be appended to the amplicons, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. A skilled artisan will understand that additional or alternative sequences used by other sequencing instruments or technologies are also equally applicable for use in the aforementioned methods as the current methods are not limited to any particular sequencing platform.

In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze the barcoded analyte or moiety. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods.

In some embodiments, a capture probe capture domain is blocked prior to adding a second probe oligonucleotide to a cell, e.g., a cell in a biological sample. This prevents the capture probe capture domain from prematurely hybridizing to the capture domain.

In some embodiments, a blocking probe is used to block or modify the free 3' end of the capture probe capture domain. In some embodiments, a blocking probe can be hybridized to the capture probe capture domain of the second probe to mask the free 3' end of the capture probe capture domain. In some embodiments, a blocking probe can be a hairpin probe or partially double stranded probe. In some embodiments, the free 3' end of the capture probe capture domain of the second probe can be blocked by chemical modification, e.g., addition of an azidomethyl group as a chemically reversible capping moiety such that the capture probes do not include a free 3' end. Blocking or modifying the capture probe capture domain, particularly at the free 3' end of the capture probe capture domain, prior to contacting second probe with the substrate, prevents hybridization of the second probe to the capture domain (e.g., prevents the capture of a poly(A) of a capture probe capture domain to a poly(T) capture domain). In some embodiments, a blocking probe can be referred to as a capture probe capture domain blocking moiety.

In some embodiments, the blocking probes can be reversibly removed. For example, blocking probes can be applied to block the free 3' end of either or both the capture probe capture domain and/or the capture probes. Blocking interaction between the capture probe capture domain and the capture probe on the substrate can reduce non-specific capture to the capture probes. After the second probe hybridizes to the analyte and is ligated to a first probe, one or more spanning probes, or a third oligonucleotide, the blocking probes can be removed from the 3' end of the capture probe capture domain and/or the capture probe, and the ligation product can migrate to and become bound by the capture probes on the substrate. In some embodiments, the removal includes denaturing the blocking probe from capture probe capture domain and/or capture probe. In some embodiments, the removal includes removing a chemically reversible capping moiety. In some embodiments, the removal includes digesting the blocking probe with an RNase (e.g., RNase H).

In some embodiments, the blocking probes are oligo (dT) blocking probes. In some embodiments, the oligo (dT) blocking probes can have a length of 15-30 nucleotides. In some embodiments, the oligo (dT) blocking probes can have a length of 10-50 nucleotides, e.g., 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50 nucleotides. In some embodiments, the analyte capture agents can be blocked at different temperatures (e.g., 4° C. and 37° C.).

(f) Kits and Compositions

In some embodiments, also provided herein are kits and compositions that include one or more reagents to detect one or more analytes and/or one or more moieties described herein. In some instances, the kit includes a substrate comprising a plurality of capture probes comprising a spatial barcode and the capture domain. In some instances, the kit includes a plurality of probes (e.g., a first probe, a second probe, one or more spanning probes, and/or a third oligonucleotide).

A non-limiting example of a kit used to perform any of the methods described herein includes: (a) a substrate comprising a plurality of capture probes comprising a spatial barcode and a capture domain; (b) a system comprising: a plurality of first probes and second probes, wherein a first probe and a second probe each comprises sequences that are substantially complementary to an analyte, and wherein the second probe comprises a capture binding domain; and (c) instructions for performing the method of any one of the preceding claims.

Another non-limiting example of a kit used to perform any of the methods described herein includes: (a) an array comprising a plurality of capture probes; (b) a plurality of probes comprising a first probe and a second, wherein the first probe and the second probe are substantially complementary to adjacent sequences of an analyte, wherein the second probe comprises (i) a capture probe binding domain that is capable of binding to a capture domain of the capture probe and (ii) a linker sequence; (c) a plurality of enzymes comprising a ribonuclease and a ligase; and (d) instructions for performing the method of any one of the preceding claims.

Another non-limiting example of a kit used to perform any of the methods described herein includes: (a) an array comprising a plurality of capture probes; (b) a plurality of probes comprising a first probe and a second probe, wherein the first probe and the second probe are substantially complementary to adjacent sequences of an analyte, wherein the first probe includes a linker sequence, wherein the second probe comprises a capture probe binding domain that is capable of binding to a capture domain of the capture probe; (c) a plurality of enzymes comprising a ribonuclease and a ligase; and (d) instructions for performing the method of any one of the preceding claims.

EXAMPLES

Example 1: Generation of Pooled Library of Barcoded Small Molecules

Figure 10:
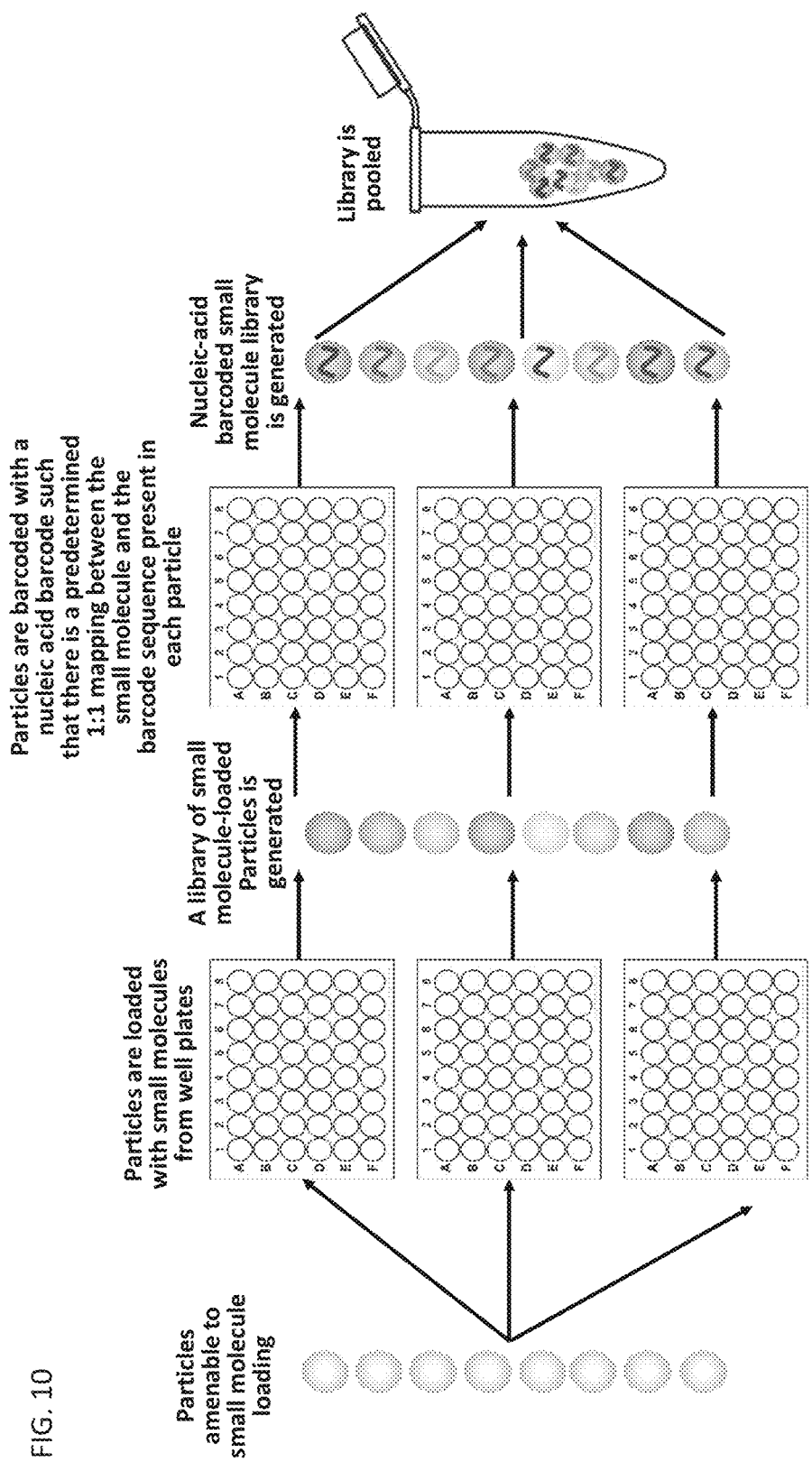
FIG. 10 is a schematic depicting the generation of barcoded small molecule libraries.

A library of small molecules with particular targets is selected. The small molecules are loaded into a 96-well plate, and particles that encapsulate the small molecules are added to each well. Particles are barcoded with a nucleic acid barcode (e.g., a moiety sequence) such that there is a predetermined 1:1 mapping between the small molecule and the barcode sequence (e.g., moiety sequence) present in each particle. After barcoding, a nucleic acid barcoded small molecule library is generated. See FIG. 10, for example.

Figure 11:
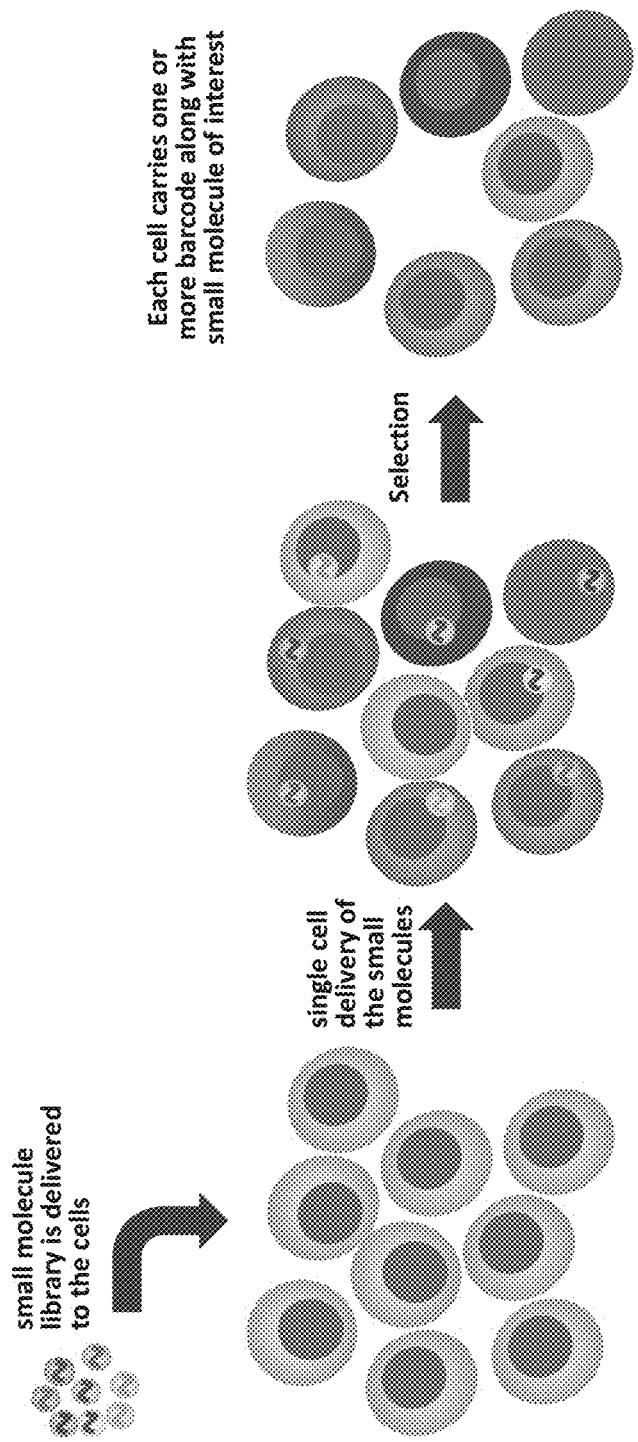
FIG. 11 is a schematic depicting multiplexed alteration of mammalian cells with a small molecule library.
Figure 12:
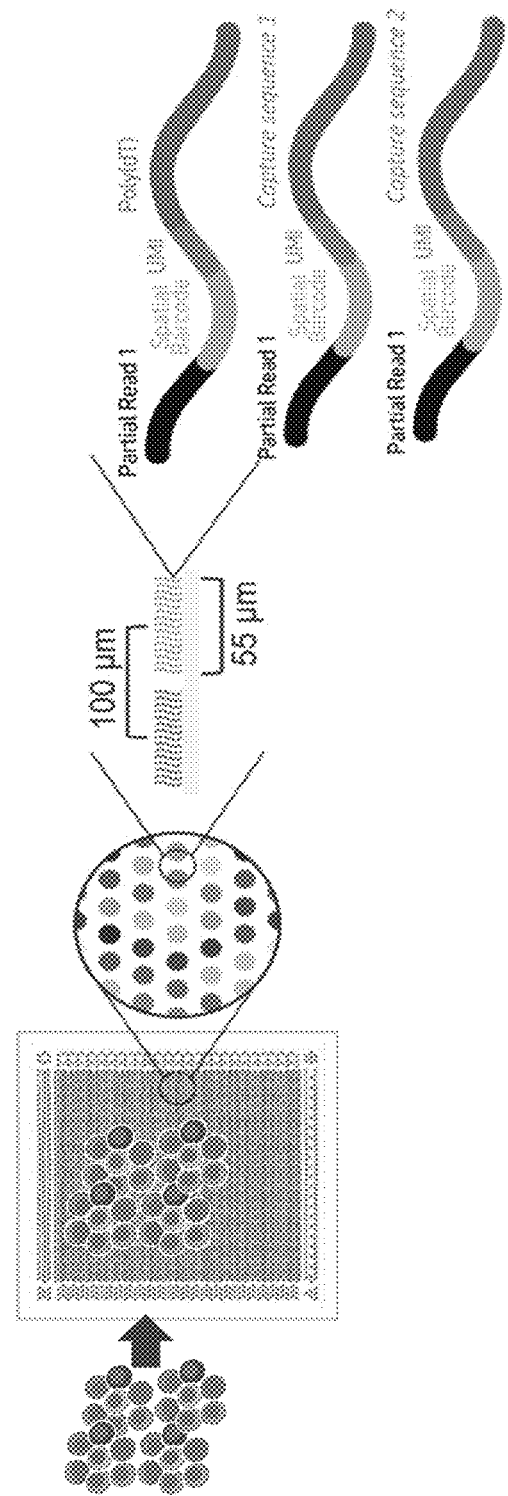
FIG. 12 is a schematic depicting programmable capture sequences that enable targeted or unbiased capture of sequences from cells comprising a small molecule.

Example 2. Method for Profiling a Biological Analyte in a Cell Comprising a Small Molecule A small molecule library of Example 1 is incubated with a cell line, allowing the small molecule to penetrate the cell. See FIG. 11, for example. Cells that uptake the small molecule are selected for, and cells including small molecules then are contacted with an array as described herein. The cells are permeabilized, allowing access to biological analytes within a cell. A biological analyte from the cell is then bound to a capture probe on the array at a distinct spatial position. The cells are removed from the array, and the bound probe is reverse transcribed. The capture probes, analytes, and sequence(s) identifying the small molecule of the cell (e.g., the second barcode or moiety sequence) are analyzed, and the biological analyte with a molecular barcode of the capture probe and sequence(s) identifying the small molecule of the cell are correlated with the distinct spatial position of the array, thus profiling the biological analyte as having been present in the cell including a small molecule. See FIG. 12, for example.

Example 3. Method for Determining the Presence or Abundance of a Moiety in a Cell Comprising a Small Molecule A small molecule library of Example 1 is incubated with a cell line, allowing the small molecule to penetrate the cell. See FIG. 11, for example. Cells that uptake the small molecule are selected for, and cells including small molecules then are contacted with an array as described herein. The cells can then be imaged. The cells are permeabilized, allowing access to the moiety sequence within a cell. A moiety sequence from the cell is then bound to a capture probe on the array at a distinct spatial position. The cells are removed from the array, and the bound probe is reverse transcribed. The capture probes and sequence(s) identifying the small molecule of the cell (e.g., moiety sequence) are analyzed and the identity of the small molecule of the cell is correlated with the distinct spatial position on the array, thus profiling the biological analyte as having been present in the cell including a small molecule. See FIG. 12, for example.

Figure 14:
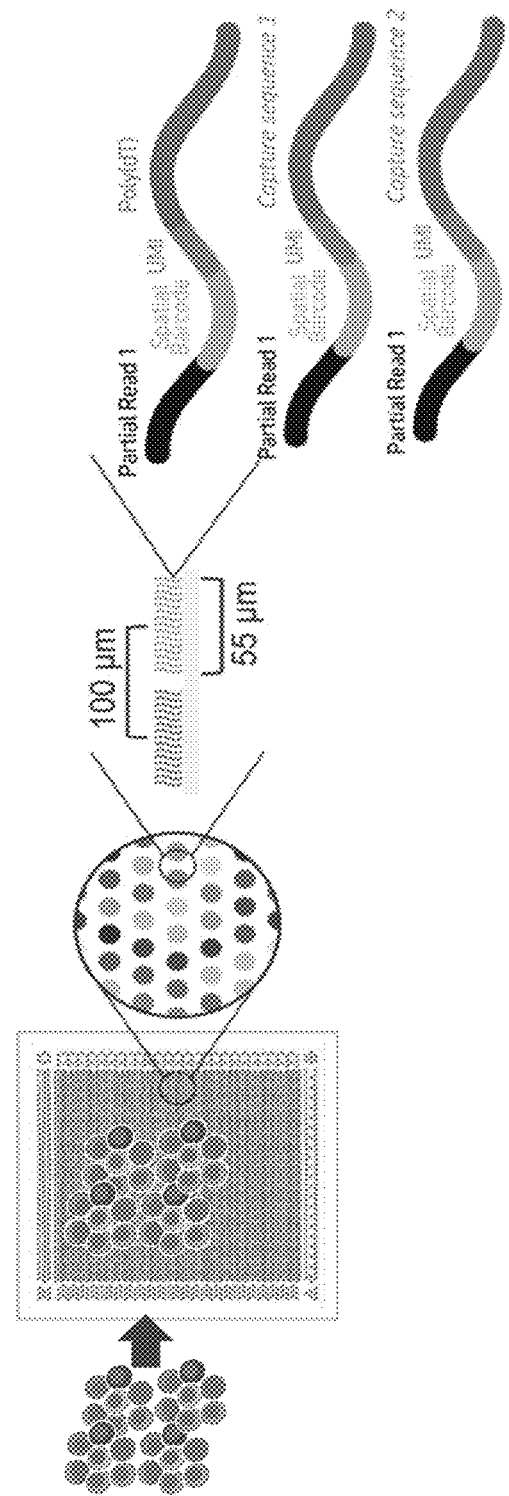
FIG. 14 is a schematic depicting programmable capture sequences that enable targeted or unbiased capture of sequences from genetically-perturbed cells.

Example 4. Method for Profiling a Biological Analyte in a Genetically Perturbed Cell A lentiviral library is selected. The lentiviral library is transduced into cells, generating a genetically-perturbed cells. See FIG. 13, for example. After selection of a particular cell including a lentiviral vector, genetically-perturbed cells are disposed on an array as described herein. The cells are permeabilized, and biological analytes are released and bound to capture probes on the array at distinct spatial positions. The cells are removed from the array, and reverse transcription/barcoding can be performed on the array. The capture probes, analytes, and sequence(s) identifying the genetic perturbation of the cell (e.g., the second barcode (e.g., moiety sequence) and/or polyadenylated gRNA) are analyzed, and the biological analyte with a molecular barcode of the capture probe and sequence(s) identifying the genetic perturbation of the cell are correlated with the distinct spatial position of the substrate, thus profiling the biological analyte as having been present in the genetically-perturbed cell. See FIG. 14, for example.

What is claimed is:

1. A method for determining presence or abundance of a nucleic acid moiety in a cell, the method comprising:
   (a) contacting the cell with an array comprising a plurality of capture probes, wherein a capture probe of the plurality of capture probes comprises: (i) a spatial barcode and (ii) a capture domain, wherein the cell comprises the nucleic acid moiety, wherein the nucleic acid moiety is a vector, and wherein the vector comprises a moiety sequence;
   (b) hybridizing the moiety sequence to the capture domain; and
   (c) determining (i) all or a part of the sequence of the moiety sequence hybridized to the capture domain, or a complement thereof, and (ii) the spatial barcode, or a complement thereof, and using the determined sequences of (i) and (ii) to determine the presence or abundance of the nucleic acid moiety in the cell.

2. The method of claim 1, wherein the moiety sequence is substantially complementary to the capture domain, optionally wherein the moiety sequence is a polyadenylated sequence.

3. The method of claim 2, wherein the nucleic acid moiety further comprises a particle introduced into the cell, wherein the particle comprises a small molecule and the moiety sequence.

4. The method of claim 3, wherein the cell is from a plurality of cells, and wherein the plurality of cells is contacted with a plurality of particles, wherein the plurality of particles comprises the particle, and wherein the cell uptakes the particle from the plurality of particles.

5. The method of claim 4, wherein the particle is a nanoparticle.

6. The method of claim 5, wherein the particle comprises gold, silica, polyethylene glycol (PEG)-poly(lactide), 1,2-distearoyl-sn-glycero-3-phosphoethanolamine-PE2000, silver, cadmium-selenide, poly(methylacrylic) acid, 1,2-distearoyl-sn-glycero-3-phosphocholine (DSPC)-cholesterol-1, 2-distearoyl-sn-glycero-3-phosphocholine (POPG), poly (lactic-co-glycolic acid) (PLGA)-polyethylene glycol, or a combination thereof.

7. The method of claim 6, wherein the particle comprises a surface modification.

8. The method of claim 7, wherein the surface modification comprises cysteine-cyan5, a cationic monolayer, a nucleic acid, poly(isobutylene-alt-maleic anhydride), a coating with fetal bovine serum (FBS), citrate, 5-aminovaleric acid, L-DOPA, melatonin, serotonin-HCl, MUS/OT, glutathione/glucose, polyethyleneimine, or a combination thereof.

9. The method of claim 3, wherein the small molecule binds to a biological target.

10. The method of claim 9, wherein the small molecule inhibits or activates the biological target.

11. The method of claim 10, wherein the biological target is a protein or a nucleic acid.

12. The method of claim 1, wherein the vector is a lentiviral vector.

13. The method of claim 12, wherein the lentiviral vector is a clustered regularly interspaced short palindromic repeats (CRISPR) lentiviral vector.

14. The method of claim 13, wherein the CRISPR lentiviral vector comprises a guide RNA (gRNA), a second barcode identifying the gRNA, or both.

15. The method of claim 14, wherein the gRNA is a single guide RNA (sgRNA).

16. The method of claim 12, wherein the lentiviral vector comprises one or more functional domains, a unique molecular identifier, a cleavage domain, or combinations thereof.

17. The method of claim 1, wherein the method further comprises:
   hybridizing an analyte from the cell to a second capture domain of a second capture probe, wherein the second capture probe comprises a second spatial barcode and the second capture domain, and wherein the second capture probe is in proximity to the capture probe that is hybridized to the moiety sequence; and
   determining (i) all or a part of a sequence of an analyte bound to the second capture domain, or a complement thereof, and (ii) the sequence of the second spatial barcode, or a complement thereof, and using the determined sequences of (i) and (ii) to determine the abundance of the analyte in the cell.

18. The method of claim 1, wherein the cell is a mammalian cell.

19. The method of claim 17, wherein the cell is permeabilized prior to hybridizing the analyte to the capture domain.

20. The method of claim 19, further comprising staining the cell prior to permeabilizing the cell.

21. The method of claim 1, further comprising imaging the cell.

22. The method of claim 21, wherein the imaging is used to determine morphology of the cell.

23. The method of claim 1, wherein the capture probe further comprises one or more functional domains, a unique molecular identifier, a cleavage domain, and combinations thereof.

24. The method of claim 23, wherein the capture domain comprises a poly-dT sequence.

* * * * *

UNITED STATES PATENT AND TRADEMARK OFFICE
CERTIFICATE OF CORRECTION

PATENT NO. : 11,732,299 B2
APPLICATION NO. : 17/153384
DATED : August 22, 2023
INVENTOR(S) : Eswar Prasad Ramachandran Iyer It is certified that error appears in the above-identified patent and that said Letters Patent is hereby corrected as shown below:

In the Claims

Column 48, Line 21, in Claim 6, delete "PE2000," and insert -- $PE_{2000}$, --.

Signed and Sealed this
Thirty-first Day of October, 2023

Katherine Kelly Vidal
*Director of the United States Patent and Trademark Office*